(12) United States Patent
Kudo

(10) Patent No.: US 10,849,738 B2
(45) Date of Patent: Dec. 1, 2020

(54) INTRAOCULAR LENS INJECTOR

(71) Applicant: Hoya Corporation, Tokyo (JP)

(72) Inventor: Kazunori Kudo, Saku (JP)

(73) Assignee: Hoya Corporation, Tokyo (JP)

( * ) Notice: Subject to any disclaimer, the term of this patent is extended or adjusted under 35 U.S.C. 154(b) by 167 days.

(21) Appl. No.: 15/756,565

(22) PCT Filed: Sep. 15, 2016

(86) PCT No.: PCT/JP2016/077327
§ 371 (c)(1),
(2) Date: Feb. 28, 2018

(87) PCT Pub. No.: WO2017/047714
PCT Pub. Date: Mar. 23, 2017

(65) Prior Publication Data
US 2018/0250125 A1 Sep. 6, 2018

(30) Foreign Application Priority Data
Sep. 16, 2015 (JP) .................................. 2015-182568

(51) Int. Cl.
*A61F 2/16* (2006.01)
(52) U.S. Cl.
CPC ................ *A61F 2/167* (2013.01); *A61F 2/16* (2013.01); *A61F 2/1672* (2013.01); *A61F 2/1678* (2013.01)
(58) Field of Classification Search
CPC ........ A61F 2/167; A61F 2/1672; A61B 17/10; A61B 10/0409
See application file for complete search history.

(56) References Cited

U.S. PATENT DOCUMENTS 2,761,446 A 9/1956 Reed
3,212,685 A 10/1965 Swan
(Continued)

FOREIGN PATENT DOCUMENTS

DE 3610925 10/1987
DE 4110278 10/1992
(Continued)

OTHER PUBLICATIONS

U.S. Appl. No. 15/126,277, filed Sep. 14, 2016, US 20170079772A1.
(Continued)

*Primary Examiner* — Alexander J Orkin
(74) *Attorney, Agent, or Firm* — Henricks Slavin LLP

(57) ABSTRACT

There is provided an intraocular lens injector configured to inject an intraocular lens having an optical portion 8 and a pair of support portions 9a, 9b, including: an injector main body 2 having a lens setting portion 6 on which the intraocular lens 7 is set; a pushing member 5 that pushes out the intraocular lens 7 from the lens setting portion 6 by moving in a direction of a central axis of the injector main body 2; and a guide slope 11 that guides the movement of the pushing member 5 when the pushing member 5 moves in the direction of the central axis of the injector main body 2, wherein when the pushing member 5 moves in the direction of the central axis of the injector main body 2, a tip end part of the pushing member 5 comes into contact with the support portions 9b of the intraocular lens 7, and comes into contact with the optical portion 8 while pushing the support portions 9b, and the guide slope 11 guides the movement of the pushing member 5 so that the tip end part of the pushing member 5 is displaced in a vertical direction.

16 Claims, 17 Drawing Sheets

(56) References Cited

U.S. PATENT DOCUMENTS

| | | |
|---|---|---|
| 4,205,747 A | 6/1980 | Gilliam et al. |
| 4,269,307 A | 5/1981 | LaHaye |
| 4,423,809 A | 1/1984 | Mazzocco |
| 4,573,998 A | 3/1986 | Mazzocco |
| 4,608,049 A | 8/1986 | Kelman |
| 4,634,423 A | 1/1987 | Bailey |
| 4,681,102 A | 7/1987 | Bartell |
| 4,697,697 A | 10/1987 | Graham et al. |
| 4,699,140 A | 10/1987 | Holmes |
| 4,702,244 A | 10/1987 | Mazzocco |
| 4,715,373 A | 12/1987 | Mazzocco et al. |
| 4,747,404 A | 5/1988 | Jampel et al. |
| 4,750,498 A | 6/1988 | Graham |
| 4,759,359 A | 7/1988 | Willis et al. |
| 4,763,650 A | 8/1988 | Hauser |
| 4,765,329 A | 8/1988 | Cumming et al. |
| 4,769,034 A | 9/1988 | Poley |
| 4,781,719 A | 11/1988 | Kelman |
| 4,787,904 A | 11/1988 | Severin |
| 4,810,249 A | 3/1989 | Haber et al. |
| 4,819,631 A | 4/1989 | Poley |
| 4,834,094 A | 5/1989 | Patton |
| 4,836,201 A | 6/1989 | Patton |
| 4,862,885 A | 9/1989 | Cumming |
| 4,880,000 A | 11/1989 | Holmes et al. |
| 4,919,130 A | 4/1990 | Stoy et al. |
| 4,934,363 A | 6/1990 | Smith et al. |
| 4,955,889 A | 9/1990 | Van Gent |
| 4,976,716 A | 12/1990 | Cumming |
| 4,988,352 A | 1/1991 | Poley |
| 4,994,028 A | 2/1991 | Leonard et al. |
| 5,066,297 A | 11/1991 | Cumming |
| 5,098,439 A | 3/1992 | Hill et al. |
| 5,123,905 A | 6/1992 | Kelman |
| 5,139,501 A | 8/1992 | Klaas |
| 5,171,241 A | 12/1992 | Buboltz et al. |
| 5,176,686 A | 1/1993 | Poley |
| 5,190,552 A | 3/1993 | Kelman |
| 5,190,553 A | 3/1993 | Kanert et al. |
| 5,222,972 A | 6/1993 | Hill et al. |
| 5,242,450 A | 9/1993 | McDonald |
| 5,259,395 A | 11/1993 | Li |
| 5,275,604 A | 1/1994 | Rheinish et al. |
| 5,281,227 A | 1/1994 | Sussman |
| 5,304,182 A | 4/1994 | Rheinish et al. |
| 5,354,333 A | 10/1994 | Kammann et al. |
| 5,395,378 A | 3/1995 | McDonald |
| 5,425,734 A | 6/1995 | Blake |
| 5,454,818 A | 10/1995 | Hambleton et al. |
| 5,468,246 A | 11/1995 | Blake |
| 5,474,562 A | 12/1995 | Orchowski et al. |
| 5,494,484 A | 2/1996 | Feingold |
| 5,496,328 A | 3/1996 | Nakajima et al. |
| 5,499,987 A | 3/1996 | Feingold |
| 5,562,676 A | 10/1996 | Brady et al. |
| 5,571,113 A | 11/1996 | McDonald |
| 5,578,042 A | 11/1996 | Cumming |
| 5,582,613 A | 12/1996 | Brady |
| 5,582,614 A | 12/1996 | Feingold |
| 5,584,304 A | 12/1996 | Brady |
| 5,616,148 A | 4/1997 | Eagles et al. |
| 5,620,450 A | 4/1997 | Eagles et al. |
| 5,643,275 A | 7/1997 | Blake |
| 5,643,276 A | 7/1997 | Zaleski |
| 5,645,534 A | 7/1997 | Chanoch |
| 5,653,715 A | 8/1997 | Reich et al. |
| 5,653,753 A | 8/1997 | Brady et al. |
| 5,702,402 A | 12/1997 | Brady |
| 5,702,441 A | 12/1997 | Zhou |
| 5,716,364 A | 2/1998 | Makker et al. |
| 5,728,075 A | 3/1998 | Levander |
| 5,728,102 A | 3/1998 | Feingold et al. |
| 5,735,858 A | 4/1998 | Makker et al. |
| 5,766,181 A | 6/1998 | Chambers et al. |
| 5,772,666 A | 6/1998 | Feingold et al. |
| 5,772,667 A | 6/1998 | Blake |
| 5,776,138 A | 7/1998 | Vidal et al. |
| 5,800,442 A | 9/1998 | Wolf et al. |
| 5,803,925 A | 9/1998 | Yang et al. |
| 5,807,400 A | 9/1998 | Chambers et al. |
| 5,810,833 A | 9/1998 | Brady et al. |
| 5,810,834 A | 9/1998 | Heyman |
| 5,860,984 A | 1/1999 | Chambers et al. |
| 5,860,986 A | 1/1999 | Reich et al. |
| 5,868,751 A | 2/1999 | Feingold |
| 5,868,752 A | 2/1999 | Makker et al. |
| 5,873,879 A | 2/1999 | Figueroa et al. |
| 5,876,406 A | 3/1999 | Wolf et al. |
| 5,876,407 A | 3/1999 | Makker et al. |
| 5,876,440 A | 3/1999 | Feingold |
| 5,891,152 A | 4/1999 | Feingold |
| 5,902,307 A | 5/1999 | Feingold et al. |
| 5,919,197 A | 7/1999 | McDonald |
| 5,921,989 A | 7/1999 | Deacon et al. |
| 5,928,245 A | 7/1999 | Wolf et al. |
| 5,941,886 A | 8/1999 | Feingold |
| 5,942,277 A | 8/1999 | Makker et al. |
| 5,944,725 A | 8/1999 | Cicenas |
| 5,947,974 A | 9/1999 | Brady et al. |
| 5,947,975 A | 9/1999 | Kikuchi et al. |
| 5,957,748 A | 9/1999 | Ichiha |
| 5,957,896 A | 9/1999 | Bendek et al. |
| 6,001,107 A | 12/1999 | Feingold |
| 6,010,510 A | 1/2000 | Brown et al. |
| 6,022,358 A | 2/2000 | Wolf et al. |
| 6,048,348 A | 4/2000 | Chambers et al. |
| 6,050,999 A | 4/2000 | Paraschac et al. |
| 6,051,000 A | 4/2000 | Heyman |
| 6,056,757 A | 5/2000 | Feingold et al. |
| 6,056,758 A | 5/2000 | Vidal et al. |
| 6,059,791 A | 5/2000 | Chambers |
| 6,074,397 A | 6/2000 | Chambers et al. |
| 6,083,230 A | 7/2000 | Makker et al. |
| 6,093,193 A | 7/2000 | Makker et al. |
| 6,129,733 A | 10/2000 | Brady et al. |
| 6,142,999 A | 11/2000 | Brady et al. |
| 6,143,000 A | 11/2000 | Feingold |
| 6,162,229 A | 12/2000 | Feingold et al. |
| 6,174,315 B1 | 1/2001 | Chambers et al. |
| 6,214,015 B1 | 4/2001 | Reich et al. |
| 6,241,737 B1 | 6/2001 | Feingold |
| 6,248,111 B1 | 6/2001 | Glick et al. |
| 6,251,114 B1 | 6/2001 | Farmer et al. |
| 6,254,607 B1 | 7/2001 | Makker et al. |
| 6,267,768 B1 | 7/2001 | Deacon |
| 6,283,975 B1 | 9/2001 | Glick et al. |
| 6,283,976 B1 | 9/2001 | Portney |
| 6,312,433 B1 | 11/2001 | Butts |
| 6,334,862 B1 | 1/2002 | Vidal et al. |
| 6,336,932 B1 | 1/2002 | Figueroa et al. |
| 6,355,046 B2 | 3/2002 | Kikuchi et al. |
| 6,371,960 B2 | 4/2002 | Heyman et al. |
| 6,386,357 B1 | 5/2002 | Egawa |
| 6,387,101 B1 | 5/2002 | Butts et al. |
| 6,398,788 B1 | 6/2002 | Makker et al. |
| 6,406,481 B2 | 6/2002 | Feingold et al. |
| 6,428,545 B2 | 8/2002 | Portney |
| 6,447,519 B1 | 9/2002 | Brady et al. |
| 6,447,520 B1 | 9/2002 | Ott et al. |
| 6,468,282 B2 | 10/2002 | Kikuchi et al. |
| 6,471,708 B2 | 10/2002 | Green |
| 6,491,697 B1 | 12/2002 | Clark et al. |
| 6,497,708 B1 | 12/2002 | Cumming |
| 6,500,181 B1 | 12/2002 | Portney |
| 6,506,195 B2 | 1/2003 | Chambers et al. |
| 6,537,283 B2 | 3/2003 | Van Noy |
| 6,540,754 B2 | 4/2003 | Brady |
| 6,554,839 B2 | 4/2003 | Brady |
| 6,558,395 B2 | 5/2003 | Hjertman et al. |
| 6,605,093 B1 | 8/2003 | Blake |
| 6,607,537 B1 | 8/2003 | Binder |
| 6,629,979 B1 | 10/2003 | Feingold |
| 6,666,871 B2 | 12/2003 | Kikuchi et al. |
| 6,679,891 B2 | 1/2004 | Makker et al. |

(56) References Cited

U.S. PATENT DOCUMENTS

| | | |
|---|---|---|
| 6,685,740 B2 | 2/2004 | Figueroa et al. |
| 6,712,848 B1 | 3/2004 | Wolf et al. |
| 6,723,104 B2 | 4/2004 | Ott |
| 6,733,507 B2 | 5/2004 | McNicholas et al. |
| 6,793,674 B2 | 9/2004 | Zapata |
| 6,858,033 B2 | 2/2005 | Kobayashi |
| 6,921,405 B2 | 7/2005 | Feingold et al. |
| 6,923,815 B2 | 8/2005 | Brady et al. |
| 6,976,989 B1 | 12/2005 | Vincent |
| 7,014,641 B2 | 3/2006 | Kobayashi et al. |
| 7,025,782 B2 | 4/2006 | Kobayashi et al. |
| 7,033,366 B2 | 4/2006 | Brady |
| 7,037,312 B2 | 5/2006 | Kikuchi et al. |
| 7,074,227 B2 | 7/2006 | Portney |
| 7,097,649 B2 | 8/2006 | Meyer |
| 7,131,976 B2 | 11/2006 | Kobayashi et al. |
| 7,156,854 B2 | 1/2007 | Brown et al. |
| 7,348,038 B2 | 3/2008 | Makker et al. |
| 7,422,604 B2 | 9/2008 | Vaquero et al. |
| 7,429,263 B2 | 9/2008 | Vaquero et al. |
| 7,458,976 B2 | 12/2008 | Peterson et al. |
| 7,476,230 B2 | 1/2009 | Ohno et al. |
| 7,494,505 B2 | 2/2009 | Kappelhof et al. |
| 7,645,300 B2 | 1/2010 | Tsai |
| 8,273,122 B2 | 9/2012 | Anderson |
| 8,382,769 B2 | 2/2013 | Inoue |
| 8,460,311 B2 | 6/2013 | Ishii |
| 8,470,032 B2 | 6/2013 | Inoue et al. |
| 8,475,526 B2 | 7/2013 | Pynson |
| 8,475,528 B2 | 7/2013 | Ichinohe et al. |
| 8,523,877 B2 | 9/2013 | Ichinohe et al. |
| 8,523,941 B2 | 9/2013 | Ichinohe et al. |
| 8,535,375 B2 | 9/2013 | Ichinohe et al. |
| 8,545,512 B2 | 10/2013 | Ichinohe et al. |
| 8,574,239 B2 | 11/2013 | Ichinohe et al. |
| 8,603,103 B2 | 12/2013 | Kudo et al. |
| 8,647,382 B2 | 2/2014 | Kudo et al. |
| 8,702,795 B2 | 4/2014 | Shoji et al. |
| 8,747,465 B2 | 6/2014 | Someya et al. |
| 8,968,328 B2 | 3/2015 | Ichinohe et al. |
| 9,114,006 B2 | 8/2015 | Inoue |
| 9,114,007 B2 | 8/2015 | Ichinohe et al. |
| 9,186,246 B2 | 11/2015 | Inoue |
| 9,220,593 B2 | 12/2015 | Ichinohe |
| 9,289,288 B2 | 3/2016 | Someya et al. |
| 9,314,373 B2 | 4/2016 | Kudo et al. |
| 9,326,847 B2 | 5/2016 | Sanger |
| 9,364,320 B2 | 6/2016 | Ichinohe et al. |
| 9,554,894 B2 | 1/2017 | Inoue |
| 9,572,710 B1 | 2/2017 | Kudo et al. |
| 9,655,718 B2 | 5/2017 | Kudo |
| 9,687,340 B2 | 6/2017 | Anderson |
| 9,877,826 B2 | 1/2018 | Kudo et al. |
| 9,901,442 B2 | 2/2018 | Kudo et al. |
| 9,907,647 B2 | 3/2018 | Inoue |
| 9,998,081 B2 | 5/2018 | Kudo et al. |
| 10,039,668 B2 | 8/2018 | Kudo et al. |
| 10,383,723 B2 | 8/2019 | Kudo |
| 10,390,940 B2 | 8/2019 | Someya et al. |
| 10,405,971 B2 | 9/2019 | Someya et al. |
| 10,517,717 B2 | 12/2019 | Inoue |
| 2001/0007942 A1 | 7/2001 | Kikuchi et al. |
| 2002/0103490 A1 | 8/2002 | Brady |
| 2002/0151904 A1 | 10/2002 | Feingold et al. |
| 2002/0165610 A1 | 11/2002 | Waldock |
| 2002/0193805 A1 | 12/2002 | Ott et al. |
| 2003/0036765 A1 | 2/2003 | Van Noy |
| 2003/0040755 A1 | 2/2003 | Meyer |
| 2003/0050647 A1 | 3/2003 | Brady |
| 2003/0088253 A1 | 5/2003 | Seil |
| 2003/0139749 A1 | 7/2003 | Kikuchi et al. |
| 2003/0181921 A1 | 9/2003 | Jeannin |
| 2003/0195522 A1 | 10/2003 | McNicholas |
| 2003/0212406 A1 | 11/2003 | Kobayashi et al. |
| 2003/0212407 A1 | 11/2003 | Kikuchi |
| 2003/0212408 A1 | 11/2003 | Kobayashi |
| 2003/0212409 A1 | 11/2003 | Kobayashi et al. |
| 2004/0111094 A1 | 6/2004 | Meyer |
| 2004/0117012 A1 | 6/2004 | Vincent |
| 2004/0127911 A1 | 7/2004 | Figueroa |
| 2004/0147938 A1 | 7/2004 | Dusek et al. |
| 2004/0186428 A1 | 9/2004 | Ray |
| 2004/0238392 A1 | 12/2004 | Peterson et al. |
| 2004/0243141 A1 | 12/2004 | Brown et al. |
| 2005/0033308 A1 | 2/2005 | Callahan et al. |
| 2005/0049605 A1 | 3/2005 | Vaquero et al. |
| 2005/0049606 A1 | 3/2005 | Vaquero et al. |
| 2005/0055011 A1 | 3/2005 | Enggaard |
| 2005/0125000 A1 | 6/2005 | Tourrette et al. |
| 2005/0143750 A1 | 6/2005 | Vaquero |
| 2005/0182419 A1 | 8/2005 | Tsai |
| 2005/0222578 A1 | 10/2005 | Vaquero |
| 2005/0261703 A1 | 11/2005 | Feingold et al. |
| 2006/0085013 A1 | 4/2006 | Dusek |
| 2006/0142781 A1 | 6/2006 | Pynson et al. |
| 2006/0167466 A1 | 7/2006 | Dusek |
| 2006/0200167 A1 | 9/2006 | Peterson et al. |
| 2006/0229633 A1 | 10/2006 | Shepherd |
| 2006/0235429 A1 | 10/2006 | Lee et al. |
| 2006/0293694 A1 | 12/2006 | Futamura |
| 2007/0005135 A1 | 1/2007 | Makker et al. |
| 2007/0270945 A1 | 11/2007 | Kobayashi |
| 2008/0033449 A1 | 2/2008 | Cole et al. |
| 2008/0058830 A1 | 3/2008 | Cole et al. |
| 2008/0086146 A1 | 4/2008 | Ishii et al. |
| 2008/0097459 A1 | 4/2008 | Kammerlander et al. |
| 2008/0221584 A1 | 9/2008 | Downer |
| 2009/0036898 A1 | 2/2009 | Ichinohe |
| 2009/0043313 A1 | 2/2009 | Ichinohe |
| 2009/0112223 A1 | 4/2009 | Downer et al. |
| 2009/0125034 A1 | 5/2009 | Pynson |
| 2009/0138022 A1 | 5/2009 | Tu et al. |
| 2009/0204122 A1 | 8/2009 | Ichinohe et al. |
| 2009/0216244 A1 | 8/2009 | Pynson |
| 2009/0248031 A1* | 10/2009 | Ichinohe ............... A61F 9/0017 606/107 |
| 2009/0270876 A1 | 10/2009 | Hoffmann et al. |
| 2009/0292293 A1* | 11/2009 | Bogaert ............... A61F 2/1664 606/107 |
| 2010/0094309 A1 | 4/2010 | Hboukhny et al. |
| 2010/0106160 A1 | 4/2010 | Tsai |
| 2010/0161049 A1 | 6/2010 | Inoue |
| 2010/0185206 A1 | 7/2010 | Ichinohe et al. |
| 2010/0217273 A1 | 8/2010 | Someya et al. |
| 2010/0286704 A1 | 11/2010 | Ichinohe et al. |
| 2010/0331808 A1 | 12/2010 | Py et al. |
| 2011/0046633 A1 | 2/2011 | Pankin et al. |
| 2011/0046635 A1 | 2/2011 | Pankin et al. |
| 2011/0082463 A1 | 4/2011 | Inoue |
| 2011/0098717 A1 | 4/2011 | Inoue |
| 2011/0144654 A1 | 6/2011 | Isaacs et al. |
| 2011/0172676 A1 | 7/2011 | Chen |
| 2011/0264101 A1 | 10/2011 | Inoue et al. |
| 2011/0270264 A1 | 11/2011 | Shoji et al. |
| 2011/0288557 A1 | 11/2011 | Kudo et al. |
| 2012/0022548 A1 | 1/2012 | Zacharias |
| 2012/0022549 A1 | 1/2012 | Someya et al. |
| 2012/0071887 A1 | 3/2012 | Ichinohe et al. |
| 2012/0123438 A1 | 5/2012 | Horvath et al. |
| 2013/0006259 A1 | 1/2013 | Sanger |
| 2013/0018460 A1 | 1/2013 | Anderson |
| 2013/0085507 A1 | 4/2013 | Nagasaka |
| 2013/0226193 A1 | 8/2013 | Kudo et al. |
| 2013/0245635 A1 | 9/2013 | Inoue |
| 2013/0345713 A1 | 12/2013 | Cole et al. |
| 2014/0081284 A1 | 3/2014 | Ichinohe et al. |
| 2014/0107660 A1 | 4/2014 | Ichinohe et al. |
| 2014/0114323 A1 | 4/2014 | Kudo et al. |
| 2014/0135784 A1 | 5/2014 | Maroscheck |
| 2014/0180299 A1 | 6/2014 | Ichinohe et al. |
| 2014/0180300 A1 | 6/2014 | Ichinohe et al. |
| 2014/0194890 A1 | 7/2014 | Kudo et al. |
| 2014/0276901 A1 | 9/2014 | Auld |
| 2015/0327992 A1 | 11/2015 | Wagner et al. |

(56) References Cited

U.S. PATENT DOCUMENTS

| | | |
|---|---|---|
| 2016/0000556 A1 | 1/2016 | Perera |
| 2016/0113759 A1 | 4/2016 | Inoue |
| 2016/0151150 A1 | 6/2016 | Sato |
| 2016/0193038 A1 | 7/2016 | Kudo et al. |
| 2016/0256316 A1 | 9/2016 | Van Noy et al. |
| 2016/0270907 A1 | 9/2016 | Attinger |
| 2016/0331587 A1 | 11/2016 | Yamada et al. |
| 2016/0346077 A1 | 12/2016 | Someya et al. |
| 2017/0079772 A1 | 3/2017 | Kudo |
| 2017/0151056 A1 | 6/2017 | Inoue |
| 2017/0202662 A1 | 7/2017 | Someya et al. |
| 2017/0252149 A1 | 9/2017 | Kudo et al. |
| 2017/0252150 A1 | 9/2017 | Kudo et al. |
| 2017/0258582 A1 | 9/2017 | Kudo et al. |
| 2017/0354493 A1 | 12/2017 | Andersen et al. |
| 2018/0353287 A1 | 12/2018 | Kudo et al. |
| 2019/0151078 A1 | 5/2019 | Watanabe et al. |
| 2019/0192284 A1 | 6/2019 | Watanabe et al. |
| 2020/0113674 A1 | 4/2020 | Someya et al. |

FOREIGN PATENT DOCUMENTS

| | | |
|---|---|---|
| DE | 19544119 A1 | 5/1997 |
| EP | 0363213 | 4/1990 |
| EP | 0727966 | 9/2003 |
| EP | 1360947 A1 | 11/2003 |
| EP | 1832247 A1 | 9/2007 |
| EP | 1338254 | 12/2008 |
| EP | 2074961 A1 | 7/2009 |
| EP | 2255751 A1 | 12/2010 |
| EP | 2286763 A1 | 2/2011 |
| EP | 2286764 A1 | 2/2011 |
| EP | 2574308 A2 | 4/2013 |
| EP | 2853236 A2 | 4/2015 |
| FR | 2749752 A | 12/1997 |
| JP | 63-197453 A | 8/1988 |
| JP | 4-212350 A | 8/1992 |
| JP | 5-103808 | 4/1993 |
| JP | 5-103809 | 4/1993 |
| JP | 8-024282 A | 1/1996 |
| JP | 8-505540 | 6/1996 |
| JP | 9-506285 A | 6/1997 |
| JP | 11-113939 A | 4/1999 |
| JP | 11-506357 A | 6/1999 |
| JP | 2000-516487 A | 12/2000 |
| JP | 2000-516488 A | 12/2000 |
| JP | 2001-502563 | 2/2001 |
| JP | 2001-104347 A | 4/2001 |
| JP | 2002-516709 A | 6/2002 |
| JP | 2002-355268 A | 12/2002 |
| JP | 2002-541912 A | 12/2002 |
| JP | 2003-144480 A | 5/2003 |
| JP | 3412106 B2 | 6/2003 |
| JP | 2003-210498 A | 7/2003 |
| JP | 2003-325569 A | 11/2003 |
| JP | 2003-325570 A | 11/2003 |
| JP | 2003-325572 A | 11/2003 |
| JP | 2004-024854 A | 1/2004 |
| JP | 2004-188194 A | 7/2004 |
| JP | 2004-351196 A | 12/2004 |
| JP | 2006-181269 A | 7/2006 |
| JP | 2006-297146 A | 11/2006 |
| JP | 2006-333924 A | 12/2006 |
| JP | 2006-333981 A | 12/2006 |
| JP | 2007-503872 A | 3/2007 |
| JP | 2007-152010 A | 6/2007 |
| JP | 2007-181604 A | 7/2007 |
| JP | 2007-244570 A | 9/2007 |
| JP | 2007-526091 A | 9/2007 |
| JP | 2007-307168 A1 | 11/2007 |
| JP | 2008-521535 A | 6/2008 |
| JP | 2008-212689 A | 9/2008 |
| JP | 2014-050484 A | 3/2014 |
| JP | 2016-137122 A | 8/2016 |
| WO | WO9407436 A1 | 4/1994 |
| WO | WO9513022 A1 | 5/1995 |
| WO | WO9628122 A1 | 9/1996 |
| WO | WO9715253 A1 | 5/1997 |
| WO | WO9812969 A1 | 4/1998 |
| WO | WO9958086 A1 | 11/1999 |
| WO | WO9959668 A1 | 11/1999 |
| WO | WO0045746 A1 | 8/2000 |
| WO | WO0062712 A1 | 10/2000 |
| WO | WO2002071982 A1 | 9/2002 |
| WO | WO2002096322 A1 | 12/2002 |
| WO | WO2005023154 A1 | 3/2005 |
| WO | WO2005070341 A1 | 8/2005 |
| WO | WO2005084588 A1 | 9/2005 |
| WO | WO2006070628 A1 | 7/2006 |
| WO | WO2006080191 A1 | 8/2006 |
| WO | WO2006090531 A1 | 8/2006 |
| WO | WO2007037223 A1 | 4/2007 |
| WO | WO2007097221 A1 | 4/2007 |
| WO | WO2007080869 A1 | 7/2007 |
| WO | WO2008149794 A1 | 12/2008 |
| WO | WO2008149795 A1 | 12/2008 |
| WO | WO2009058929 A1 | 7/2009 |
| WO | WO2009148091 A1 | 12/2009 |
| WO | WO2011126144 A1 | 10/2011 |
| WO | WO2011155636 A1 | 12/2011 |
| WO | WO2012086797 A1 | 6/2012 |
| WO | WO2012155887 A1 | 11/2012 |
| WO | WO2015012312 A1 | 1/2015 |

OTHER PUBLICATIONS

U.S. Appl. No. 16/313,180, filed Dec. 26, 2018.
U.S. Appl. No. 16/313,184, filed Dec. 26, 2018.
U.S. Appl. No. 16/550,144, filed Aug. 23, 2019.
U.S. Appl. No. 15/063,395, filed Mar. 7, 2016, US 20160346077A1.
U.S. Appl. No. 15/476,717, filed Mar. 31, 2017, US 20170202662A1.
EPO Extended European Search Report dated May 14, 2019 for EPO App. Ser. No. 16846585.4.
U.S. Appl. No. 15/888,078, filed Feb. 4, 2018.
U.S. Appl. No. 15/071,880, filed Mar. 16, 2016, US 20160193038A1.
U.S. Appl. No. 15/870,979, filed Jan. 14, 2018.
U.S. Appl. No. 15/756,565, filed Feb. 28, 2018.
U.S. Appl. No. 15/756,569, filed Feb. 28, 2018.
PCT Search Report dated Dec. 13, 2016 for PCT App. Ser. No. PCT/JP2016/077327.
U.S. Appl. No. 12/602,442, filed Dec. 15, 2009, U.S. Pat. No. 8,747,465.
U.S. Appl. No. 13/244,449, filed Sep. 24, 2011, U.S. Pat. No. 9,289,288.
U.S. Appl. No. 15/063,395, filed Mar. 7, 2016, U.S. Pat. No. 10,390,940.
U.S. Appl. No. 15/476,717, filed Mar. 31, 2017, U.S. Pat. No. 10,405,971.
U.S. Appl. No. 16/550,144, filed Aug. 23, 2019, US 20200113674A1.
U.S. Appl. No. 12/602,454, filed Dec. 15, 2009, U.S. Pat. No. 8,475,528.
U.S. Appl. No. 13/244,452, filed Sep. 24, 2011, U.S. Pat. No. 8,535,375.
U.S. Appl. No. 12/667,510, filed Dec. 31, 2009, U.S. Pat. No. 9,114,006.
U.S. Appl. No. 14/812,104, filed Jul. 29, 2015, U.S. Pat. No. 9,907,647.
U.S. Appl. No. 12/995,263, filed Dec. 15, 2010, U.S. Pat. No. 9,554,894.
U.S. Appl. No. 15/382,377, filed Dec. 16, 2016, US 20170151056A1.
U.S. Appl. No. 12/997,651, filed Dec. 13, 2010, U.S. Pat. No. 8,382,769.
U.S. Appl. No. 13/757,790, filed Feb. 2, 2012, U.S. Pat. No. 9,186,246.
U.S. Appl. No. 13/583,216, filed Apr. 6, 2011, U.S. Pat. No. 9,326,847.
U.S. Appl. No. 13/699,708, filed Jun. 8, 2011, U.S. Pat. No. 8,647,382.
U.S. Appl. No. 14/145,846, filed Dec. 31, 2013, U.S. Pat. No. 9,314,373.

(56) References Cited

OTHER PUBLICATIONS

U.S. Appl. No. 15/071,880, filed Mar. 16, 2016, U.S. Pat. No. 10,039,668.
U.S. Appl. No. 15/336,678, filed Oct. 27, 2016, U.S. Pat. No. 9,572,710.
U.S. Appl. No. 15/608,895, filed May 30, 2017, U.S. Pat. No. 9,980,811.
U.S. Appl. No. 13/059,401, filed Feb. 16, 2011, U.S. Pat. No. 8,702,795.
U.S. Appl. No. 13/061,143, filed Feb. 26, 2011, U.S. Pat. No. 8,470,032.
U.S. Appl. No. 13/143,322, filed Jul. 5, 2011, U.S. Pat. No. 8,603,103.
U.S. Appl. No. 14/099,989, filed Dec. 8, 2013, U.S. Pat. No. 9,655,718.
U.S. Appl. No. 15/600,679, filed May 19, 2017, U.S. Pat. No. 9,877,826.
U.S. Appl. No. 15/600,684, filed May 19, 2017, U.S. Pat. No. 9,901,442.
U.S. Appl. No. 11/814,508, filed Jul. 23, 2007, U.S. Pat. No. 8,545,512.
U.S. Appl. No. 14/033,888, filed Sep. 23, 2013, U.S. Pat. No. 9,220,593.
U.S. Appl. No. 11/816,676, filed Aug. 20, 2007, U.S. Pat. No. 8,523,877.
U.S. Appl. No. 13/966,209, filed Aug. 13, 2013, U.S. Pat. No. 9,364,320.
U.S. Appl. No. 12/095,172, filed May 28, 2008, U.S. Pat. No. 8,523,941.
U.S. Appl. No. 14/011,018, filed Aug. 27, 2013, U.S. Pat. No. 8,968,328.
U.S. Appl. No. 12/088,328, filed Mar. 27, 2008, U.S. Pat. No. 8,574,239.
U.S. Appl. No. 14/065,365, filed Oct. 28, 2013, U.S. Pat. No. 9,114,007.
U.S. Appl. No. 11/722,601, filed Apr. 10, 2008, U.S. Pat. No. 8,460,311.
U.S. Appl. No. 15/126,277, filed Sep. 14, 2016, U.S. Pat. No. 10,383,723.
U.S. Appl. No. 15/756,565, filed Feb. 28, 2018, US 20180250125A1.
U.S. Appl. No. 15/756,569, filed Feb. 28, 2018, US 20180353287A1.
U.S. Appl. No. 16/313,180, filed Dec. 26, 2018, US 20190192284A1.
U.S. Appl. No. 16/313,184, filed Dec. 26, 2018, US 20190151078A1.

\* cited by examiner

INTRAOCULAR LENS INJECTOR

TECHNICAL FIELD

The present invention relates to an intraocular lens injector used for injecting an intraocular lens into an eye.

DESCRIPTION OF RELATED ART

As one of a cataract surgery, it is widely practiced to extract a white cloudy lens by ultrasonic emulsification and suction and then inject the intraocular lens into the eye. Further, in recent years, in order to realize minimally invasive cataract surgery with less burden on an eye, a one-piece type intraocular lens made of a soft material such as silicone elastomer or soft acrylic is injected into the eye in a small folded state. The one-piece type intraocular lens has an optical portion that performs a lens function and a pair of support portions that extend from the optical portion, and an entire intraocular lens is made of a flexible material.

Further, as an intraocular lens injector for handling the one-piece type intraocular lens, there is an injector having a function of folding an intraocular lens so as to embrace a pair of support portions with an optical portion in order to improve operability for a surgeon to inject the intraocular lens as much as possible (for example, see patent document 1). In this type of intraocular lens injector, it is necessary to fold the optical portion roundly in a state that tip end parts of the respective support portions are placed on a surface of the optical portion. Further, conventional intraocular lens injectors include the one having a pushing member which pushes out an intraocular lens and which folds the intraocular lens when the intraocular lens is pushed out by the pushing member.

PRIOR ART DOCUMENT

Patent Document

[Patent Document 1] Japanese Unexamined Patent Publication No. 2011-255029

SUMMARY OF THE INVENTION

Problem to be Solved by the Invention

However, the conventional intraocular lens injector involves a problem that when the intraocular lens is pushed out by the pushing member, the tip end part of the support portion is caught on an edge of the optical portion or the like, and the tip end part of the support portion is not placed smoothly on the surface of the optical portion.

A main object of the present invention is to provide an intraocular lens injector capable of surely placing the tip end part of the support portion on the surface of the optical portion when the intraocular lens is folded so as to embrace the support portion with the optical portion.

Means for Solving the Problem

According to a first aspect, there is provided an intraocular lens injector configured to inject an intraocular lens having an optical portion and support portions extending from the optical portion into an eye, including:

an injector main body having a lens setting portion on which the intraocular lens is placed;

a pushing member that pushes out the intraocular lens from the lens setting portion by moving in a direction of a central axis of the injector main body; and a guide mechanism that guides the movement of the pushing member when the pushing member moves in the direction of the central axis of the injector main body, wherein when the pushing member moves in the direction of the central axis of the injector main body, a tip end part of the pushing member comes into contact with the support portions of the intraocular lens, and comes into contact with the optical portion while pushing the support portions, and the guide mechanism guides the movement of the pushing member so that the tip end part of the pushing member is displaced in a direction intersecting the central axis of the injector main body.

According to a second aspect of the present invention, there is provided the intraocular lens injector of the first aspect, wherein the guide mechanism includes a guide slope that guides the movement of the pushing member, and the tip end part of the pushing member is displaced in a vertical direction along the guide slope.

According to a third aspect of the present invention, there is provided the intraocular lens injector of the second aspect, wherein the guide mechanism guides the movement of the pushing member so that the tip end part of the pushing member pushes the support portions while being displaced upward.

According to a fourth aspect of the present invention, there is provided the intraocular lens injector of the second or third aspect, wherein the guide mechanism includes:

a lower guide slope having an inclined portion inclined obliquely upward from an upstream side to a downstream side in a moving direction of the pushing member; and an upper guide slope having an inclined portion inclined obliquely downward from the upstream side to the downstream side in the moving direction of the pushing member.

According to a fifth aspect of the present invention, there is provided the intraocular lens injector of any one of the second to fourth aspects, wherein the guide mechanism includes a restraining portion that suppresses a lateral shake of the tip end part of the pushing member that moves in the direction of the central axis of the injector main body.

According to a sixth aspect of the present invention, there is provided the intraocular lens injector of the first aspect, wherein the guide mechanism has a guide groove for guiding the movement of the pushing member, and the tip end part of the pushing member is displaced in a left-right direction along the guide groove.

According to a seventh aspect of the present invention, there is provided the intraocular lens injector of the sixth aspect, wherein the guide mechanism guides the movement of the pushing member, so that the tip end part of the pushing member comes into contact with the tip end part of the support portions at a position deviated from the position of the central axis of the injector main body in one of the left and right directions, and thereafter the tip end part of the pushing member is displaced to the other side in the left-right direction and comes into contact with the optical portion at the position of the central axis of the injector main body.

According to an eighth aspect of the present invention, there is provided the intraocular lens injector of any one of the first to seventh aspects, further including:

a pair of left and right side wall guides that guide the movement of the optical portion of the intraocular lens pushed out from the lens setting portion by the pushing member, wherein the pair of left and right side wall guides have a guide surface for guiding the optical portion of the intraocular lens pushed out from the lens setting portion by the pushing member, and have a protrusion for temporarily stopping the optical portion moving along the guide surface.

According to a ninth aspect of the present invention, there is provided the intraocular lens injector of the eighth aspects, wherein a movement start position at which the optical portion of the intraocular lens starts moving is set in the lens setting portion, and the protrusion is disposed so as to come into contact with the optical portion when the optical portion is moved by a predetermined amount from the movement start position.

According to a tenth aspect of the present invention, there is provided the intraocular lens injector of the ninth aspect, wherein the predetermined amount is 0.5 mm or more and 1.0 mm or less.

According to an eleventh aspect of the present invention, there is provided the intraocular lens injector of any one of the eighth to tenth aspects, wherein a protruding dimension of the protrusion is 0.1 mm or more and 0.5 mm or less.

According to a twelfth aspect of the present invention, there is provided the intraocular lens injector of any one of the first to eleventh aspects, wherein the intraocular lens is a pre-load type in which the intraocular lens is preset on the lens setting portion.

According to a thirteenth aspect of the present invention, there is provided the intraocular lens injector of any one of the first to twelfth aspects, wherein the intraocular lens is set on the lens setting portion in a no-load state.

Advantage of the Invention

According to the present invention, when folding the intraocular lens so as to embrace the support portions with the optical portion, the tip end part of the support portions can be securely placed on the surface of the optical portion.

BRIEF DESCRIPTION OF THE DRAWINGS

FIG. 10A is a schematic view when the upper groove is viewed from a position of a central axis of the injector main body, FIG. 10B is a schematic view when the lower groove is viewed from the position of the central axis of the injector main body, FIG. 10C is a view showing a sectional structure of the upper groove at a position V1-V1 of FIG. 10A, and FIG. 10D is a view showing the sectional structure of the lower groove at a position V2-V2 of FIG. 10B.

FIG. 16A is a view of the internal structure of the joint portion viewed from above, and FIG. 16B is a perspective view of the internal structure of the joint portion viewed from backside.

FIG. 18A is a view of the internal structure of the joint portion viewed from above, and FIG. 18B is a perspective view of the internal structure of the joint portion viewed from the backside.

DETAILED DESCRIPTION OF THE INVENTION

Figure 1:
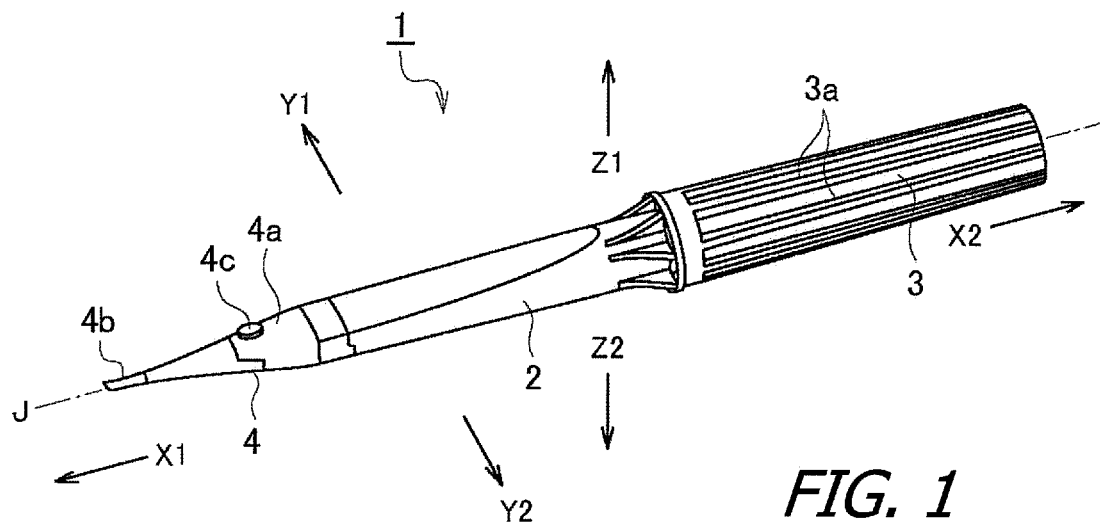
FIG. 1 is a perspective view showing an overall structure of an intraocular lens injector according to an embodiment of the present invention.

Embodiments of the present invention will be described hereafter in detail, with reference to the drawings.

In the embodiment of the present invention, explanation will be given in the following order.

1. Structure of an intraocular lens injector
2. Method for assembling the intraocular lens injector
3. How to use the intraocular lens injector
4. Effect of the embodiment
5. Other embodiment
6. Modified example, etc.

1. Structure of an Intraocular Lens Injector

Figure 2:
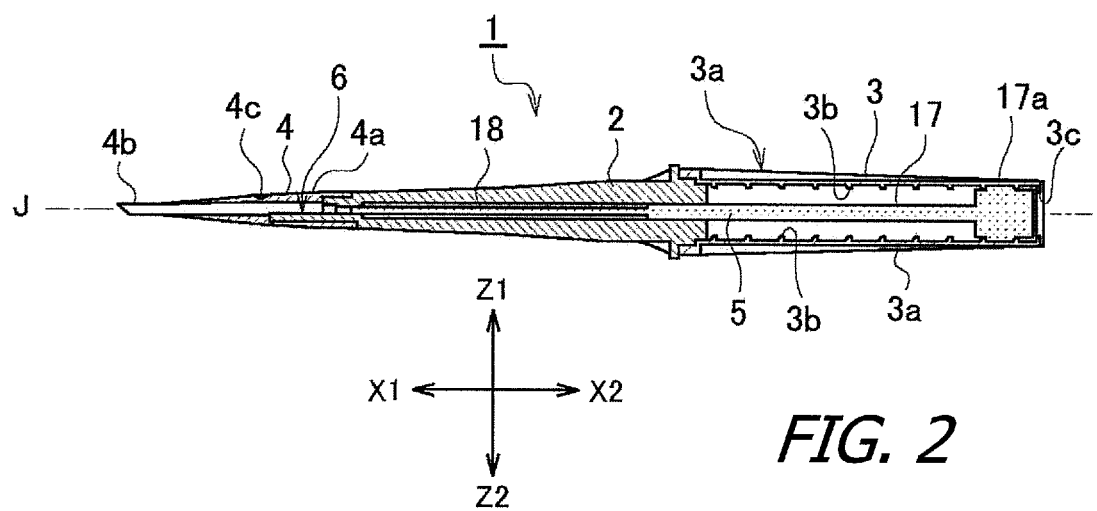
FIG. 2 is a side sectional view showing the overall structure of the intraocular lens injector according to an embodiment of the present invention.

FIG. 1 is a perspective view showing an overall structure of an intraocular lens injector according to an embodiment of the present invention, and FIG. 2 is a side sectional view showing the overall structure of the intraocular lens injector according to an embodiment of the present invention.

An intraocular lens injector 1 shown in the figure is provided as a disposable product, and is used when injecting the intraocular lens into the eye. The intraocular lens injector 1 is of a preload type in which an intraocular lens is preset. In the preload type intraocular lens injector 1, the intraocular lens is preset on the lens setting portion described later in the stage of shipping the intraocular lens injector 1 from a factory.

In this embodiment, in order to clarify a relative positional relationship and a direction of movement and the like of each part of the intraocular lens injector 1, X1 direction is set as a tip end side (front side), X2 direction is set as a rear end side (rear side), Y1 direction is set as a right side (right side), Y2 direction is set as a left side (left side), Z1 direction is set as an upper side (upper side), and Z2 direction is set as a lower side (lower side). Among them, the X1 direction and the X2 direction correspond to a direction of a central axis of the intraocular lens injector 1 (hereinafter also referred to simply as a "central axis direction"), and the Y1 direction and the Y2 direction correspond to a width direction (left-right direction) of the intraocular lens injector 1, and the Z1 direction and the Z2 direction correspond to a height direction (vertical direction) of the intraocular lens injector 1. Further, a plane parallel to the X1 direction, the X2 direction, the Y1 direction and the Y2 direction is set as a horizontal plane, and a plane perpendicular to the horizontal plane is set as a vertical plane. Reference symbol J in the figure indicates the central axis of the intraocular lens injector 1.

Figure 3:
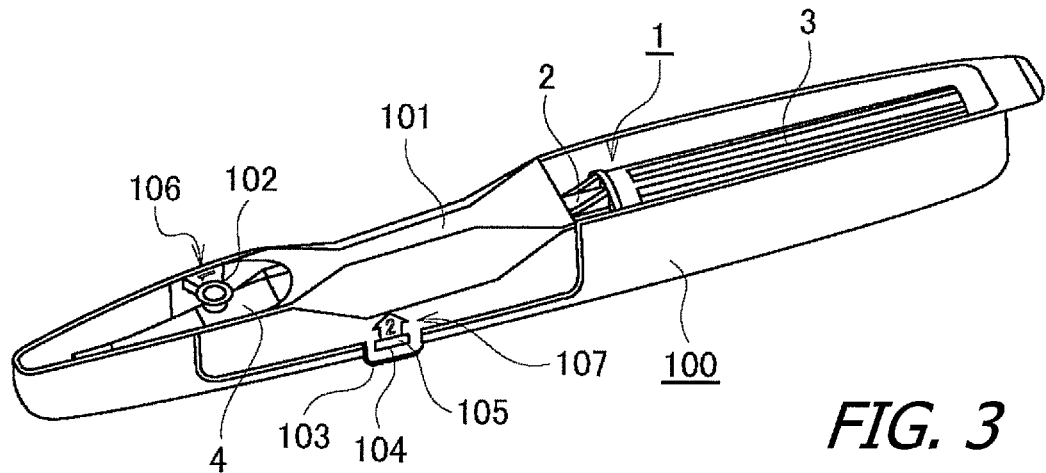
FIG. 3 is a perspective view showing a state in which the intraocular lens injector of the embodiment of the present invention is housed in a case.

As shown in FIG. 3, for example, the intraocular lens injector 1 is provided to a user in a state of being housed in a case 100. The case 100 is made of resin. The case 100 is structured to open upward so that the intraocular lens injector 1 can be attached and detached. The case 100 is formed with an opening/closing cover 101 for partially closing an upper part of the case 100 and an injection cover 102 for opening/closing together with the opening/closing cover 101.

Figure 4:
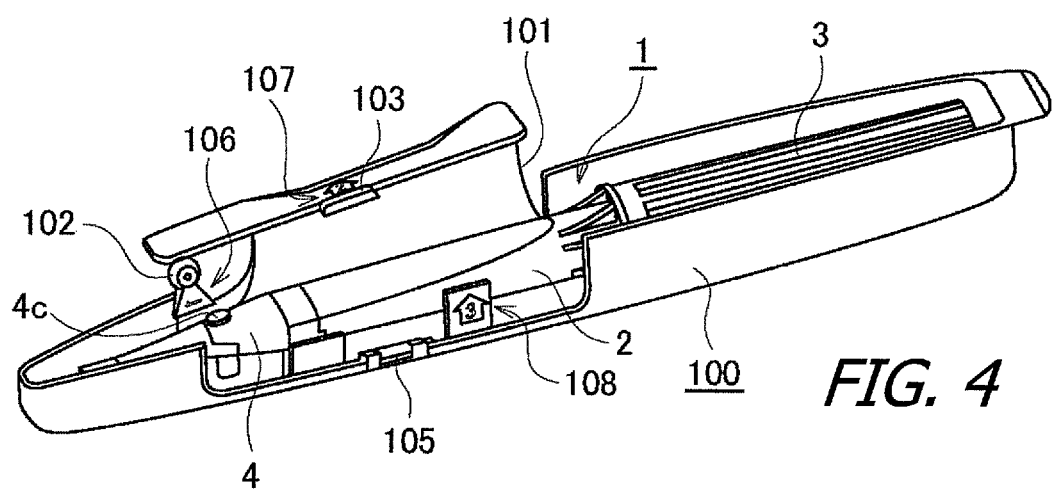
FIG. 4 is a perspective view showing a state in which the intraocular lens injector of the embodiment of the present invention is taken out from the case.

The case 100 has a space capable of housing the intraocular lens injector 1, in which the intraocular lens injector 1 is housed. When the intraocular lens injector 1 is housed in the case 100, the opening/closing cover 101 is in a closed state (FIG. 3), and when the intraocular lens injector 1 is taken out from the case 100, the opening/closing cover 101 is in an open state (FIG. 4). When the opening/closing cover 101 is in a closed state, the intraocular lens injector 1 housed in the case 100 is pressed from above by the opening/closing cover 101. When the opening/closing cover 101 is in an open state, the upper part of the case 100 is opened. An opening/closing operation of the opening/closing cover 101 is performed by a manufacturer or the user of the intraocular lens injector 1.

The opening/closing cover 101 includes a hooking portion 103. The hooking portion 103 is a portion for hooking a user's finger when opening/closing the opening/closing cover 101. Further, a slit 104 is formed in the opening/closing cover 101. The slit 104 is formed in the vicinity of the hooking portion 103. In contrast, a protrusion 105 is formed in the case 100 as shown in FIG. 4. The protrusion 105 is engaged with the slit 104 when the opening/closing cover 101 is closed, thereby holding the opening/closing cover 101 in a closed state.

The injection lid 102 is for injecting a viscoelastic substance. A small hole is formed in the injection lid 102, and a part of the injection lid 102 is formed in a funnel shape around this hole. The injection lid 102 is partially connected to the opening/closing cover 101 so as to move together with the opening/closing cover 101.

Further, the case 100 is marked with numbers 106, 107, and 108. Numbers attached to each of the marks 106, 107, and 108 indicate procedures of work to be performed by the user when taking out the intraocular lens injector 1 from the case 100. Further, arrows attached to the marks 107 and 108 indicate directions of work to be performed by the user. Specifically, the mark 106 with the number "1" attached thereto, indicates that the operation of injecting the viscoelastic substance through the injection lid 102 should be performed. Further, the mark 107 with the numeral "2" attached thereto, indicates that the operation of opening the opening/closing cover 101 in the direction of the arrow should be performed, and the mark 108 with the numeral "3" attached thereto, indicates that the operation of taking out the intraocular lens injector 1 in the direction of the arrow should be performed.

As shown in FIGS. 1 and 2, the intraocular lens injector 1 roughly includes an injector main body 2, an operation part 3, an injection tube 4, and a pushing member 5. Each part of the intraocular lens injector 1 is made of resin.

Injector Main Body

The injector main body 2 is formed in a tubular shape as a whole. A hollow portion that allows the movement of the pushing member 5 in the X1 direction and the X2 direction is formed inside of the injector main body 2. A lens setting portion 6 is provided at a tip end part of the injector main body 2. The lens setting portion 6 is formed so as to protrude forward from an outer circumferential wall on a lower side of the injector main body 2. The intraocular lens 7 is set on the lens setting portion 6 (see FIGS. 5A to 5C). A central axis J of the intraocular lens injector 1 coincides with each central axis of the injector main body 2, the operation part 3, and the injection tube 4.

In this embodiment, as an example, one-piece type intraocular lens 7 made of a soft material such as silicone elastomer or soft acrylic is to be handled. The intraocular lens 7 has an optical portion 8 that performs an optical function and a pair (two) support portions 9a, 9b extending outwardly from the outer peripheral edge of the optical portion 8 in an arc shape. The optical portion 8 is formed in a circular shape in plan view. Each of the pair of support portions 9a, 9b is formed in an elongated arm shape.

Figure 5A:
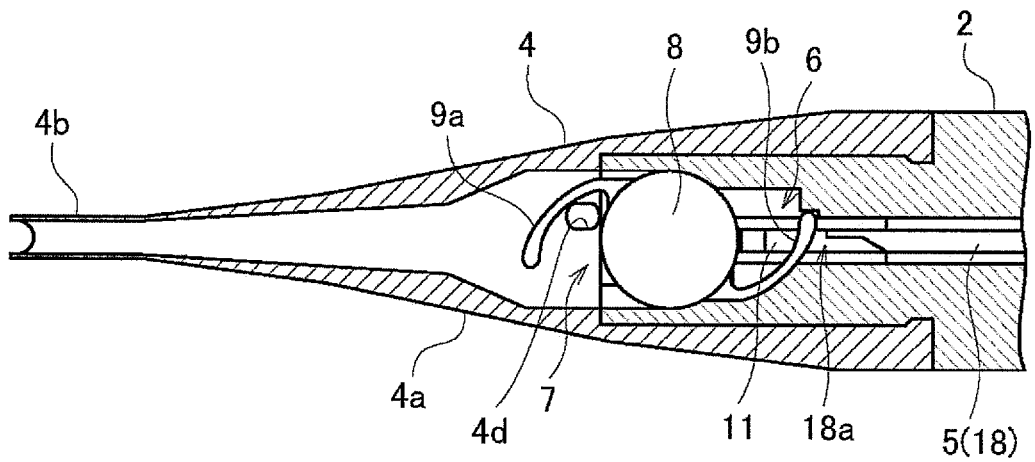
FIG. 5(A) FIG. 5A is a plan sectional view showing a structure of an essential part of the intraocular lens injector according to an embodiment of the present invention.
Figure 5B:
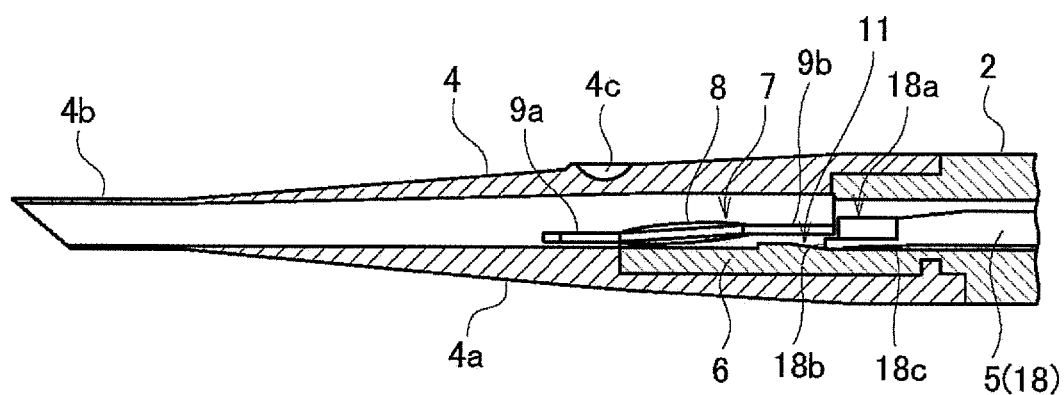
FIG. 5B is a side sectional view showing the structure of the essential part.

Here, the structure of the lens setting portion 6 will be described in detail with reference to FIGS. 5A to 5C.

A guide slope 11 is formed on an upper surface of the lens setting portion 6. The guide slope 11 constitutes a guide mechanism for guiding the movement of the pushing member 5 when the pushing member 5 moves in the central axis direction of the injector main body 2. The guide slope 11 is formed on a moving path of the pushing member 5 in a state in which a part of the lens setting portion 6 is protruded (raised) upward. As shown in FIG. 5C, the guide slope 11 has an inclined portion 11a inclined with respect to a horizontal plane, a top portion 11b not inclined, and a step portion 11c perpendicular to the horizontal plane. The inclined portion 11a is inclined in a state in which the inclined portion 11a gradually becomes higher from the back of the lens setting portion 6 toward the front. In other words, the inclined portion 11a is inclined obliquely upward from the upstream side to the downstream side in the moving direction of the pushing member 5. The top portion 11b is formed to extend horizontally from an uppermost portion of the inclined portion 11a. The step portion 11c is formed in a state of falling vertically from the tip end of the top portion 11b.

Further, in order to limit an amount of a vertical displacement of the intraocular lens 7 set on the lens setting portion 6, a pair of right and left recessed grooves (not shown) are formed in the lens setting portion 6. The pair of recessed grooves are formed on the left and right side walls defining the lens setting portion 6 of the injector main body 2 so as to face each other. When the intraocular lens 7 is set on the lens setting portion 6, the pair of recessed grooves are engaged with the left and right outer peripheral parts of the optical portion 8, thereby restricting the vertical movement of the optical portion 8.

The intraocular lens 7 is set on the lens setting portion 6 having the abovementioned structure, in a state in which one of the support portions 9a is disposed in front of the lens setting portion 6 and the other support portion 9b is disposed behind the lens setting portion 6. Further, the intraocular lens 7 is approximately horizontally set (placed) on the lens setting portion 6 in a state in which a rear edge of the optical portion 8 faces the step portion 11c of the guide slope 11. In FIG. 2, the notation of the intraocular lens 7 is omitted.

Operation Portion

The operation portion 3 is coaxially connected to the rear end part of the injector main body 2. In this connected state, the operation portion 3 is supported so as to be rotatable around the central axis of the injector main body 2. The operation portion 3 is formed into a tubular shape. A plurality of protrusions 3a are formed on the outer peripheral surface of the operation portion 3. Each protrusion 3a is formed in parallel to a longitudinal direction of the operation portion 3. The operation portion 3 is a portion rotated by a user such as an operator when the intraocular lens 7 is pushed out using the pushing member 5. At this time, by forming a plurality of protrusions 3a on the outer periphery of the operation portion 3, the fingers of the user are caught on the protrusions 3a, and therefore it is easy to rotate the operation portion 3. In this specification, a state before rotating the operation portion 3 by a user is referred to as an initial state, which is a state of the intraocular lens injector 1.

As shown in FIG. 2, a first screw portion 3b is formed on the inner peripheral surface of the operation portion 3. The first screw portion 3b constitutes a female screw. The first screw portion 3b is formed substantially throughout the central axis direction of the operation portion 3. An abutting portion 3c is formed at a rear end part of the operation portion 3. The abutting portion 3c is formed by bending inward so as to narrow an opening diameter of the rear end part of the operation portion 3. The abutting portion 3c is a portion where the rear end part of a plunger portion 17 abuts so that the plunger portion 17 does not protrude rearward from the rear end part of the operation portion 3.

Injection Tube

An injection tube 4 functions to guide the intraocular lens 7 set on the lens setting portion 6 into an eye in a state that the intraocular lens 7 is folded into a small size when the intraocular lens 7 is injected into the eye. The injection tube 4 integrally has a hollow injection tube main body 4a and a narrow tubular nozzle portion 4b. The injection tube 4 is attached to a tip end part of the injector main body 2. In this attachment state, the lens setting portion 6 of the injector main body 2 is housed in the injection tube main body 4a of the injection tube 4. The space inside of the injection tube main body 4a is gradually narrowed toward the nozzle portion 4b, for small folding of the intraocular lens 7 pushed out from the lens setting portion 6 to the injection tube 4. The intraocular lens 7 is finally rounded and folded so as to embrace the pair of support portions 9a and 9b with the optical portion 8.

The nozzle portion 4b is formed at the tip end part of the injection tube 4. The tip end part of the nozzle portion 4b opens with an oblique incision. Therefore, the opening of the nozzle portion 4b faces obliquely downward. The tip end part of the nozzle portion 4b is a portion to be inserted into an incisional wound of the eyeball when the intraocular lens 7 is injected into the eye using the intraocular lens injector 1.

An injection portion 4c is formed on an upper wall of the injection tube main body 4a, and a through hole 4d is formed on a lower wall of the injection tube main body 4a. The injection portion 4c is a portion for injecting a viscoelastic substance (for example, sodium hyaluronate etc.). The through hole 4d is a portion into which a pin (not shown) provided vertically erect on the bottom of the abovementioned case 100 is inserted. Such a pin is disposed to protrude through the through hole 4d in the vicinity of a base end portion of the support portion 9b, when the intraocular lens injector 1 incorporating the intraocular lens 7 therein, is housed in the case 100. Thereby, in a state in which the intraocular lens injector 1 is housed in the case 100, the movement of the intraocular lens 7 is suppressed so that the position of the intraocular lens 7 does not largely deviate in the lens setting portion 6.

Pushing Member

The pushing member 5 is provided movably in the central axis direction of the injector main body 2. The pushing member 5 functions to push out the intraocular lens 7 form the lens setting portion 6 by moving in the central axis direction (X1 direction) of the injector main body 2. At this time, the pushing member 5 moves in the hollow portion formed by the injector main body 2, the operation portion 3, and the injection tube 4.

The pushing member 5 has the plunger portion 17 and a rod portion 18. The plunger portion 17 and the rod portion 18 may constitute the pushing member 5 in a unitary structure, or the plunger portion 17 and the rod portion 18 may have separate structures and they may be mutually assembled to constitute the pushing member 5. The plunger portion 17 is disposed relatively rearwardly, and the rod portion 18 is disposed relatively forward in the direction of the central axis of the intraocular lens injector 1. Therefore, the tip end part of the pushing member 5 corresponds to the tip end part of the rod portion 18.

The plunger portion 17 is formed into a rod shape. In the initial state before use, the plunger portion 17 is disposed in a state of being inserted into the operation portion 3 so as not to protrude from the rear end part of the operation portion 3. A second screw portion 17a is formed at the rear end part of the plunger portion 17. The second screw portion 17a constitutes a male screw. The second screw portion 17a is engaged with the first screw portion 3b inside of the operation portion 3. When the intraocular lens injector 1 is used, the operation portion 3 is operated so as to rotate around the central axis of the injector main body 2, thereby moving the entire pushing member 5 in a forward direction. A movement start position of the plunger portion 17 at that time is uniquely determined by abutting the rear end part of the plunger portion 17 against the abutting portion 3c of the operation portion 3.

The pushing member 5 moves in the central axis direction of the injector main body 2, and in this state, the rod portion 18 functions to release the intraocular lens 7 from the opening of the nozzle portion 4b of the injection tube 4, by pushing out the intraocular lens 7 forward, which is set on the lens setting portion 6 is pushed out. The rod portion 18 is formed into a rod shape thinner than the plunger portion 17. The rod portion 18 is configured to be elastically deformable so as to have moderate flexibility. A first contact portion 18a and a second contact portion 18b are formed at the tip end part of the rod portion 18. When the intraocular lens 7 is pushed out by the rod portion 18, the first contact portion 18a comes into contact with the support portion 9b and the second contact portion 18b comes into contact with the optical portion 8. The upper end portion of the second contact portion 18b protrudes like a canopy so as to grip the edge of the optical portion 8. The lower surface of the tip end side of the rod portion 18 is an inclined surface 18c gently inclined rearward from the second contact portion 18b. When the pushing member 5 is moved forward, the inclined surface 18c is formed to displace the tip end part of the rod portion 18 upward along the inclined portion 11a of the guide slope 11 in the middle of the movement, and thereafter displace the tip end part of the rod portion 18 downward using the inclination of the inclined surface 18c.

2. Method for Assembling the Intraocular Lens Injector

Next, a method for assembling the intraocular lens injector 1 will be described.

First, after preparing the members (2, 3, 4, 5) constituting the intraocular lens injector 1, the pushing member 5 is attached to the operation portion 3. Specifically, the tip end opening part of the operation portion 3 is engaged with the rear end part of the plunger portion 17 of the pushing member 5 so as to cover this opening part, so that the operation portion 3 is rotated. Thereby, the first screw portion 3b formed on the inner peripheral surface of the operation portion 3 and the second screw portion 17a provided at the rear end part of the plunger portion 17 are engaged with each other. Therefore, when the operation portion 3 is rotated while restricting the rotation of the pushing member 5, the plunger portion 17 is inserted into the operation portion 3 in accordance with the rotation of the operation portion 3. At this time, the operation portion 3 is rotated until the rear end part of the plunger portion 17 abuts against the abutting portion 3c of the operation portion 3.

Next, the injector main body 2 is attached to the operation portion 3. At this time, the rod portion 18 of the pushing member 5 is inserted into the hollow portion of the injector main body 2. Thereby, the tip end parts (18a, 18b) of the rod portion 18 are disposed slightly in front of the lens setting portion 6.

Next, the separately prepared intraocular lens 7 is horizontally set on the lens setting portion 6 of the injector main body 2. At this time, the optical portion 8 of the intraocular lens 7 is disposed slightly forward of the step portion 11c of the guide slope 11. Further, one support portion 9a is disposed frontward and the other support portion 9b is disposed rearward. Further, the tip end side of the support portion 9b is disposed to block the moving direction of the rod portion 18.

In the state in which the intraocular lens 7 is set on the lens setting portion 6 as described above, the intraocular lens 7 is set in a no-load state. The no-load state refers to a state in which almost no load (pressure) is applied to the intraocular lens, that is, a state in which the intraocular lens maintains its original shape. The original shape of the intraocular lens refers to the shape in the stage of finishing manufacturing the intraocular lens.

Next, the injection tube 4 is attached to the tip end part of the injector main body 2. Thus, the assembly of the intraocular lens injector 1 incorporating the intraocular lens 7 is completed. For the structure for connecting the injector main body 2 and the operation portion 3 and the structure for connecting the injector main body 2 and the injection tube 4, for example, the structure described in the specification of Japanese Patent Application No. 2014-55761 and drawings (Japanese Patent Application Laid-open No. 2015-177845) may be adopted, or any other connecting structure may be adopted.

After the assembly of the intraocular lens injector 1 is completed as described above, the intraocular lens injector 1 is housed in the case 100, and the opening/closing cover 101 is closed. At this time, the injection lid 102 of the case 100 is placed over the injection part 4c of the intraocular lens injector 1. In this state, the intraocular lens injector 1 is stored in a sterilized bag or the like together with the case 100.

3. How to Use the Intraocular Lens Injector

Next, how to use the intraocular lens injector 1 will be described.

First, the user takes out the intraocular lens injector 1 from a sterilized bag or the like together with the case 100.

Next, the user injects the viscoelastic substance from the injection lid 102 in accordance with an instruction of the mark 106. Thereby, the viscoelastic substance is injected (supplied) from the injection lid 102 through the injection portion 4c to the intraocular lens 7 set on the lens setting portion 6.

Next, the user opens the opening/closing cover 101 in accordance with the instruction of the mark 107. Then, it is possible to obtain a state in which the mark 108 hidden by the opening/closing cover 101 is visible. Therefore, the user takes out the intraocular lens injector 1 from the case 100 in accordance with the instruction of the mark 108.

Thereafter, the user pushes the intraocular lens 7 from the tip end part of the injection tube 4 by rotating the operation portion 3. The operation of each part of the intraocular lens injector 1 at that time will be described.

Movement of the Pushing Member

First, the operation of the pushing member 5 will be described when the operation portion 3 is rotated.

When the operation portion 3 is rotated in one direction, the pushing member 5 moves forward by the engagement between the first screw portion 3b and the second screw portion 17a. At this time, the plunger portion 17 of the pushing member 5 moves straight in the central axis direction (X1 direction) of the injector main body 2 while engaging with the hollow portion of the injector main body 2. Further, the pushing member 5 moves as shown in FIGS. 6A to 6D in accordance with the rotation operation of the operation portion 3.

Figure 6A:
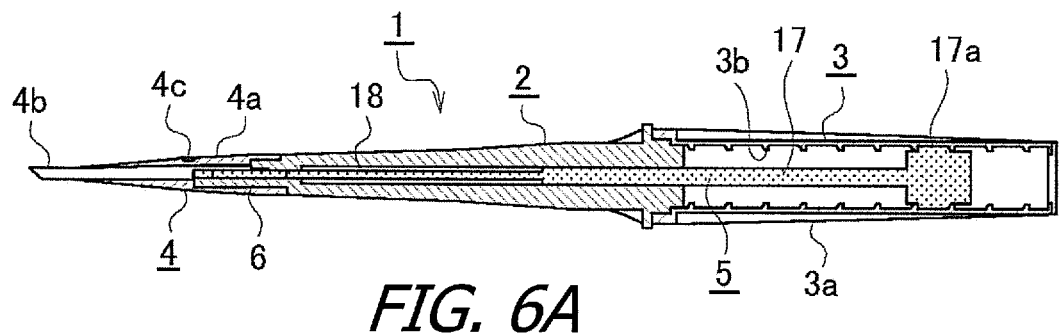
FIGS. 6A to 6D are views showing time-sequentially a state of a movement of a pushing member in accordance with a rotation operation of the operation portion.
Figure 6B:
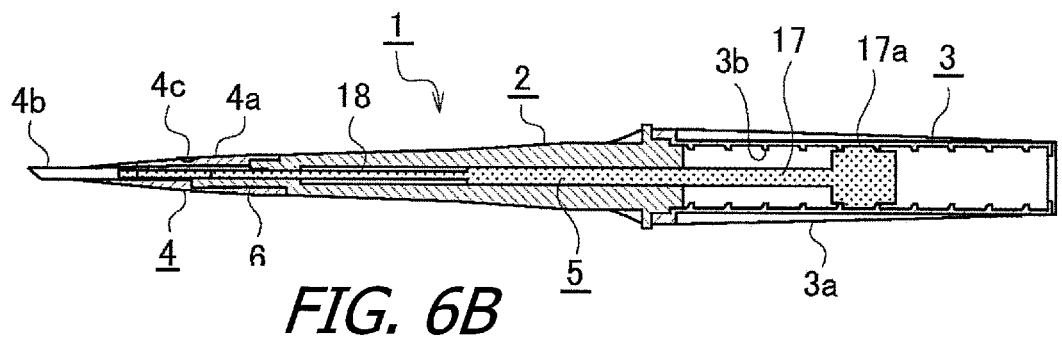
Figure 6C:
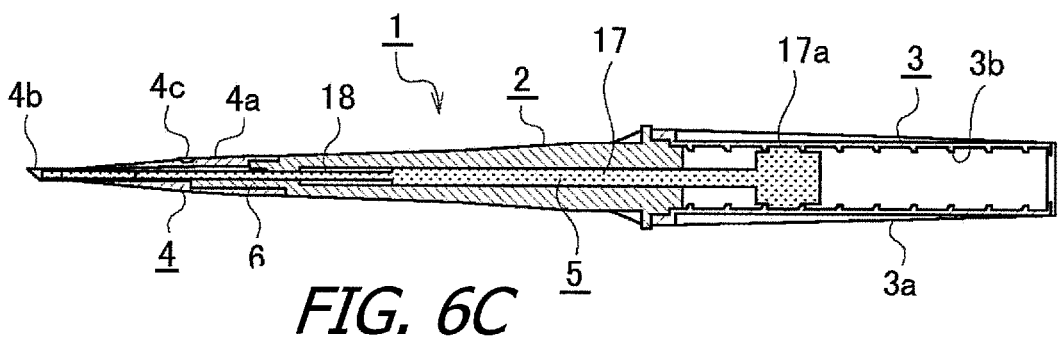
Figure 6D:
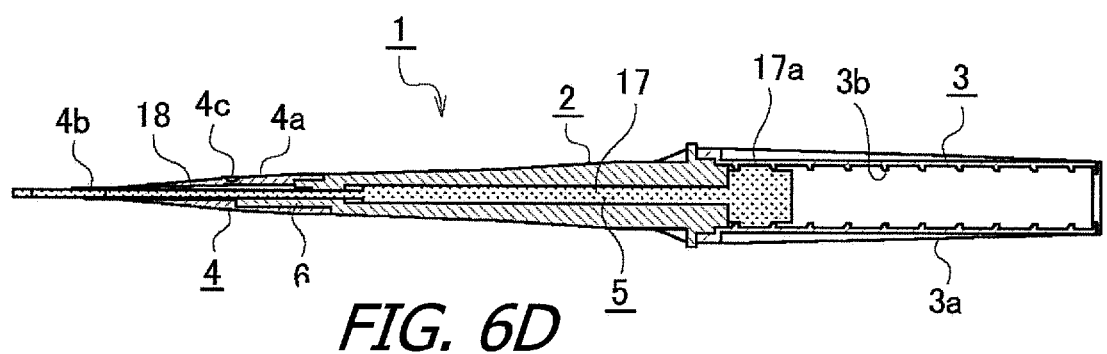

FIG. 6A shows a stage in which the tip end part of the rod portion 18 of the pushing member 5 is advanced to the tip end part of the lens setting portion 6, and FIG. 6B shows a stage in which the tip end part of the rod portion 18 is advanced to the injection tube main body 4a of the injection tube 4. Further, FIG. 6C shows a stage in which the tip end part of the rod portion 18 is advanced to the nozzle portion 4b of the injection tube 4, and FIG. 7D shows a stage in which the tip end part of the rod portion 18 protrudes forward from the nozzle portion 4b of the injection tube 4.

Movement of the Tip End of the Rod Portion and State Change of the Intraocular Lens When the pushing member 5 is moved as described above, the tip end part of the rod portion 18 moves forward so as to push out the intraocular lens 7 from the lens setting portion 6. At that time, the tip end part of the rod portion 18 pass the lens setting portion 6 mainly through four stages, by being guided by the guide slope 11. This state is shown in a plane sectional view of FIGS. 7A to 7D and a side sectional view of FIGS. 8A to 8D. Each stage will be described hereafter in detail.

First Stage

Figure 7A:
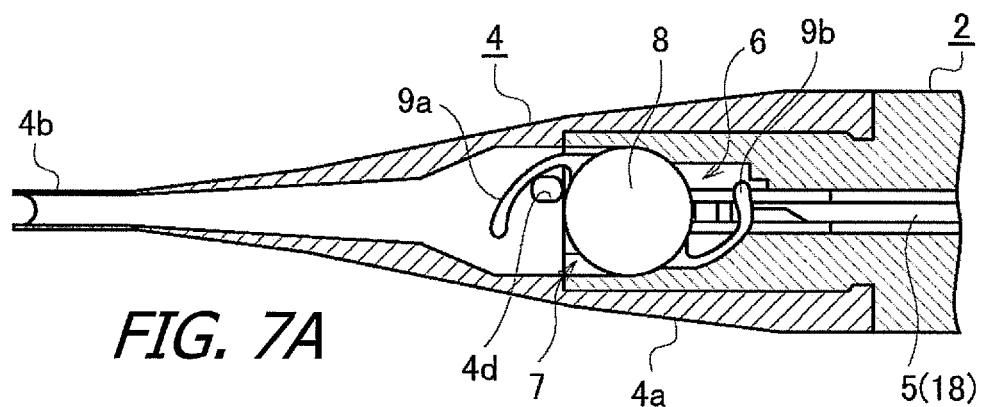
FIGS. 7A to 7D are plan sectional views showing a state in which the intraocular lens is pushed out by the pushing member, in a chronological order.
Figure 8A:
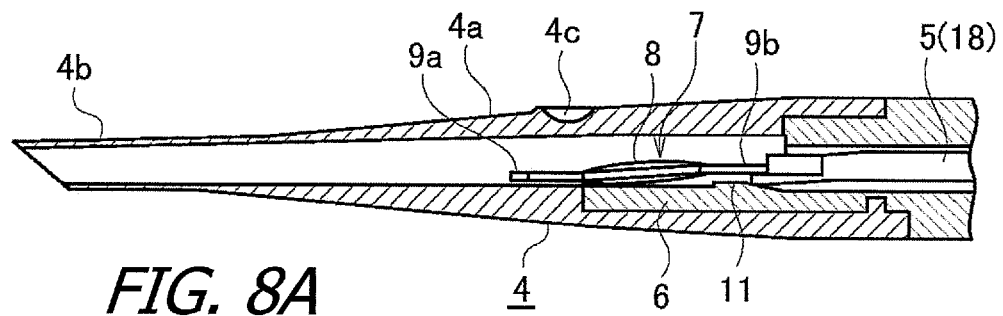
FIGS. 8A to 8D are side sectional views showing a state in which the intraocular lens is pushed out by the pushing member, in a chronological order.

The first stage is the stage in which the tip end part of the rod portion 18 comes into contact with the support portion 9b as shown in FIGS. 7A and 8A. At this time, as the tip end part of the rod portion 18 advances to the lens setting portion 6, the first contact portion 18a at the tip end of the rod portion 18 comes into contact with the tip end side of the support portion 9b. Further, the tip end side of the support portion 9b is supported in a manner of riding onto the first contact portion 18a.

Second Stage

Figure 7B:
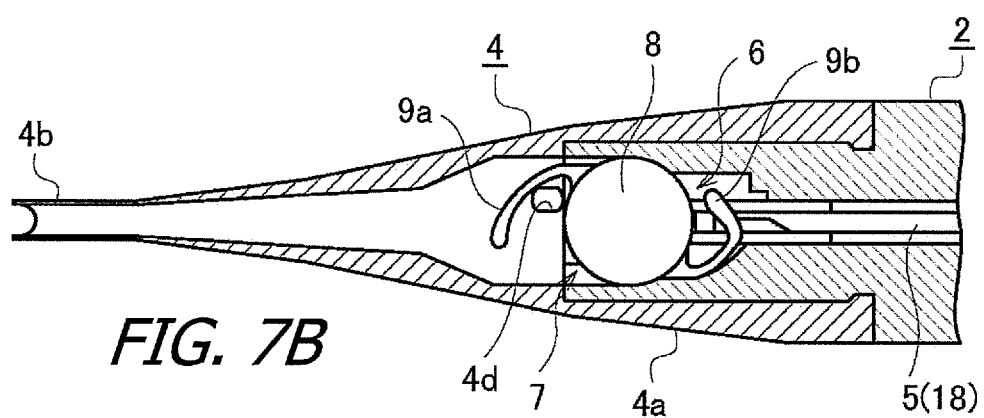
Figure 8B:
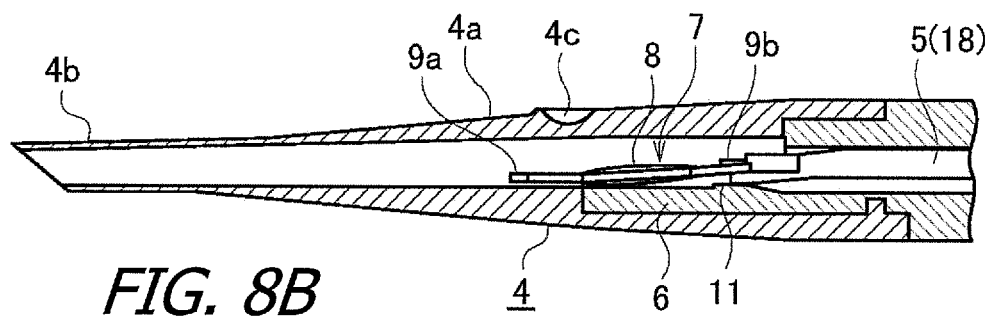

The second stage is the stage of pushing the support portion 9b while the tip end part of the rod portion 18 comes into contact with the support portion 9b, as shown in FIGS. 7B and 8B. At this time, when the tip end part of the rod portion 18 reaches the inclined portion 11a of the guide slope 11, an upward force is applied to the tip end part of the rod portion 18. Then, the tip end part of the rod portion 18 is displaced upward due to an elastic deformation of the rod portion 18 itself. Therefore, the tip end part of the rod portion 18 moves forward so as to push the support portion 9b while being displaced upward along the inclined portion 11a of the guide slope 11. Thereby, the support portion 9b is gradually bent. Further, the tip end side of the support portion 9b is gradually raised.

When the pair of support portions 9a and 9b are made of a material which is soft and easily elastically deformed, even if the support portion 9b is pushed in by the tip end part of the rod portion 18, the pushing force is absorbed by deformation of the support portion 9b. Therefore, even if the support portion 9b is pushed in by the tip end part of the rod portion 18, the position of the optical portion 8 hardly changes from an initial state.

Third Stage

Figure 7C:
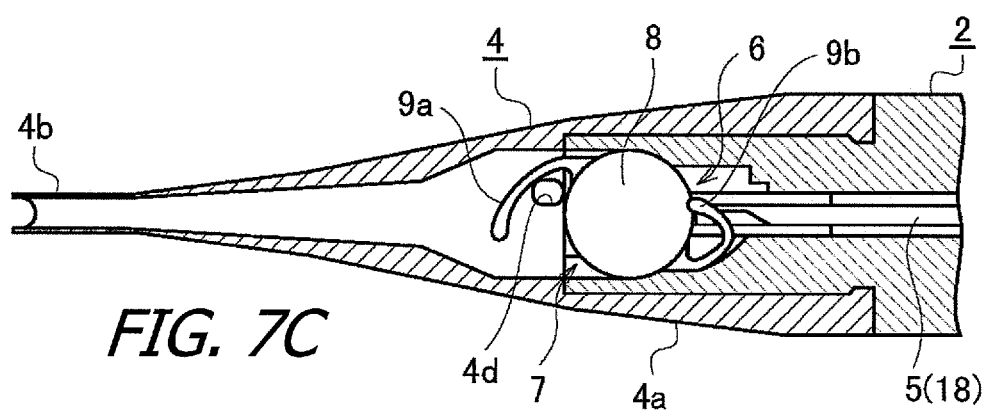
Figure 7D:
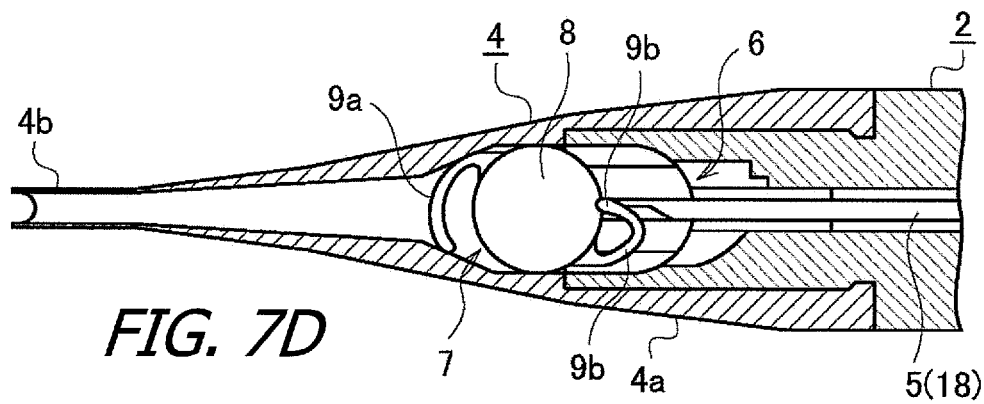
Figure 8C:
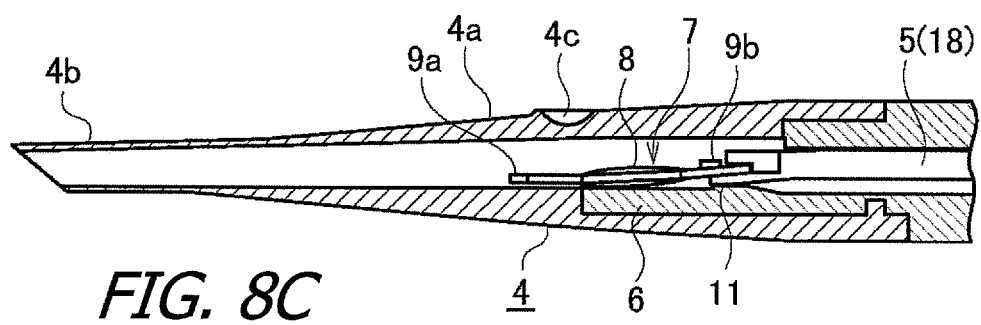

The third stage is the stage in which the tip end part of the rod portion 18 comes into contact with the optical portion 8, as shown in FIGS. 7C and 8C. At this time, the tip end part of the rod portion 18 comes into contact with the optical portion 8 by reaching the top portion 11b of the guide slope 11 and passing therethrough. Specifically, the second contact portion 18b formed at the tip end part of the rod portion 18 comes into contact with the edge of the optical portion 8. Further, the support portion 9b is further bent by the forward movement of the rod portion 18. Specifically, the support portion 9b as a whole is bent toward the optical portion 8 so as to form a substantially U-shape. Further, the tip end side of the support portion 9b is properly raised before the tip end part of the rod portion 18 comes into contact with the optical portion 8. Therefore, the tip end part of the support portion 9b is less likely to catch on the edge of the optical portion 8, and in this situation, the tip end part of the support portion 9b rides onto the surface of the optical portion 8.

Fourth Stage

Figure 8D:
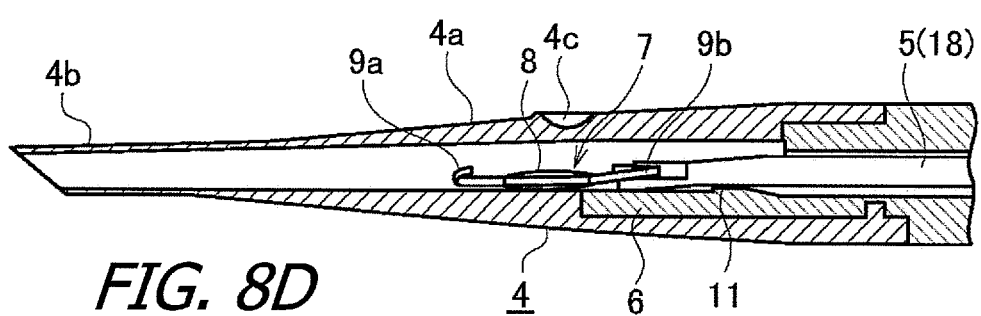

The fourth stage is the stage in which the tip end part of the rod portion 18 pushes the entire intraocular lens 7 while coming into contact with the support portion 9b and the optical portion 8, as shown in FIGS. 7D and 8D. At this time, a downward force is exerted on the tip end part of the rod portion 18 by a reaction force due to the elastic deformation of the rod portion 18 itself, and therefore the inclined surface 18c of the rod portion 18 is pushed against the edge portion (the upper end of the step portion 11c) of the lower guide slope 11. Therefore, the tip end part of the rod portion 18 is gradually displaced downward in accordance with the inclination of the inclined surface 18c immediately after passing through the step portion 11c of the guide slope 11, and finally returns to an original height position.

The intraocular lens 7 thus pushed out from the lens setting portion 6, is subsequently pushed by the rod portion 18 and moves forward in the injection tube 4. At that time, the optical portion 8 of the intraocular lens 7 is rounded from the left and right by the inner wall of the injection tube main body 4a having a tapered shape, and is finally folded so as to embrace the pair of support portions 9a, 9b. Further, the support portion 9a is bent in conformity with the shape of the gradually narrowed space in the injection tube 4 (see FIG. 7D).

The intraocular lens 7 thus folded is pushed out from the nozzle portion 4b of the injection tube 4 by the rod portion 18. At this time, by pushing out the intraocular lens 7 from the opening of the nozzle portion 4b in a state in which the nozzle portion 4b of the injection tube 4 is inserted into the incisional wound of the eyeball, the intraocular lens 7 can be injected into the eye.

4. Effect of the Embodiment

According to the embodiment of the present invention, the tip end part of the rod portion 18 is guided by the guide mechanism so as to be displaced in a direction (vertical direction in this embodiment) intersecting the central axis of the injector main body 2, when the pushing member 5 moves in the central axis direction of the injector main body 2. With this structure, when the tip end part of the rod portion 18 is sequentially brought into contact with the support portion 9b and the optical portion 8 by the movement of the pushing member 5, an appropriate height difference can be provided between the optical portion 8 and the support portion 9b. Therefore, it is possible to securely place the tip end part of the support portion 9b on the surface of the optical portion 8.

Further, according to the embodiment of the present invention, by forming the guide slope 11 in the injector main body 2 and displacing the tip end part of the rod portion 18 in the vertical direction along the guide slope 11, it is possible to raise the tip end side of the support portion 9b upward. Therefore, it is possible to create a situation in which the tip end part of the support portion 9b is easy to ride on the surface of the optical portion 8.

Further, according to the embodiment of the present invention, the tip end part of the rod portion 18 pushes the support portion 9b while being displaced upward along the inclined portion 11a of the guide slope 11. Therefore, it is possible to perform the operation of bending the support portion 9b and the operation of raising the support portion 9b in parallel in a series of pushing operations by the pushing member 5.

5. Other Embodiments

Subsequently, another embodiment of the present invention will be described. Since there are several other embodiments of the present invention, for the sake of convenience, the abovementioned embodiment (FIGS. 1 to 8D) is referred to as a first embodiment, and the other embodiments are referred to as a second embodiment, a third embodiment and the like, respectively. Further, in other embodiments of the present invention, the same reference numerals are given to the same parts as those of the embodiment (the first embodiment) described above.

Second Embodiment

A second embodiment of the present invention will be described hereafter.

In the second embodiment of the present invention, the structure of the guide mechanism for guiding the movement of the pushing member 5 is different from that of the abovementioned first embodiment. Namely, in the first embodiment, the guide slope 11 is formed on the lens setting portion 6 of the injector body 2, and the guide mechanism is constituted by this guide slope 11. In contrast, in the second embodiment, as will be described later, guide slopes are respectively provided on the upper side and the lower side of a moving path of the pushing member 5, and the guide mechanism is constituted by these guide slopes. Further, the guide mechanism of the second embodiment includes a suppressing portion for suppressing a lateral shake of the tip end part of the pushing member 5.

Figure 9:
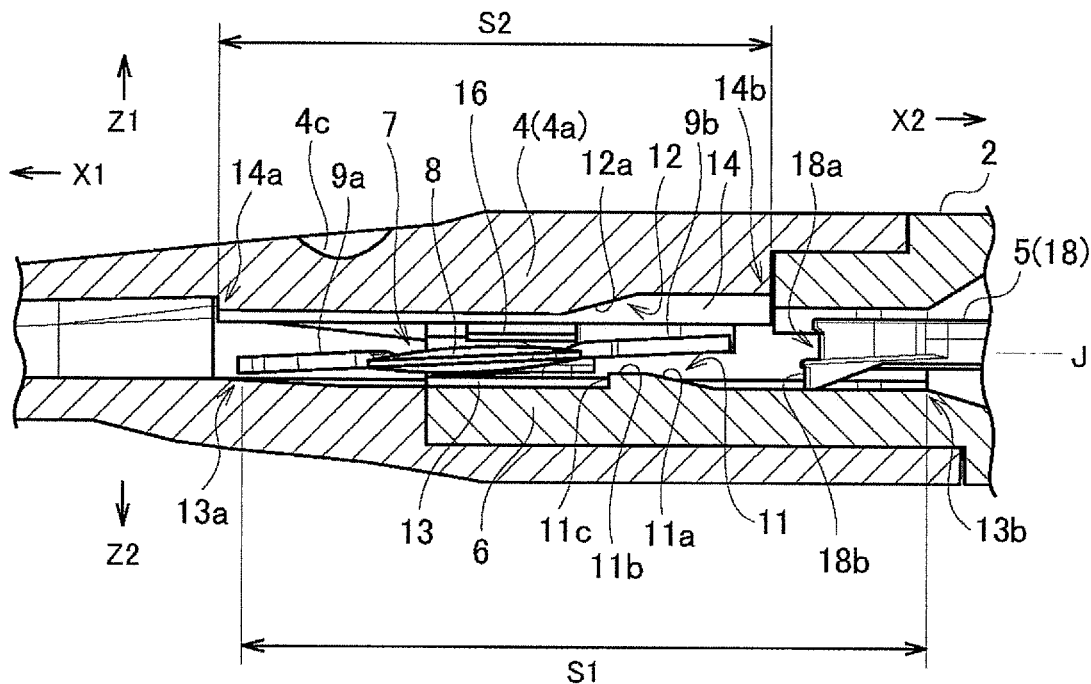
FIG. 9 is a sectional view showing an essential part of the intraocular lens injector according to a second embodiment of the present invention.

FIG. 9 is a sectional view showing an essential part of the intraocular lens injector according to the second embodiment of the present invention. FIG. 9 is a view obtained by vertically sectioning the essential part of the intraocular lens injector on the central axis J (FIG. 1), wherein a left direction corresponds to the X1 direction, a right direction corresponds to the X2 direction, an upward direction corresponds to the Z1 direction, and a downward direction corresponds to the Z2 direction in the figure.

In this second embodiment, the guide mechanism for guiding the movement of the pushing member 5 is constituted by the lower guide slope 11 and the upper guide slope 12. In the same manner as the guide slope 11 (FIGS. 5A to 5C) described in the first embodiment, the lower guide slope 11 is constituted by the inclined portion 11a, the top portion 11b and the step portion 11c. The upper guide slope 12 is constituted by the inclined portion 12a. The lower guide slope 11 is formed on the lens setting portion 6 of the injector main body 2, and the upper guide slope 12 is formed on the inner wall of the injection tube 4. Further, in the moving direction (X1 direction) of the pushing member 5, the inclined portion 12a of the upper guide slope 12 is disposed on the downstream side of the inclined portion 11a of the lower guide slope 11.

The lower guide slope 11 displaces the tip end part of the rod portion 18 of the pushing member 5 upward using the inclined portion 11a, and the upper guide slope 12 displaces the tip end part of the rod portion 18 downward using the inclined portion 12a. Therefore, the inclined portion 11a of the lower guide slope 11 is inclined obliquely upward from the upstream side toward the downstream side in the moving direction (X1 direction) of the pushing member 5, and the inclined portion 12a of the upper guide slope 12 is inclined obliquely downward from the upstream side to the downstream side in the moving direction (X1 direction) of the pushing member 5.

Further, grooves 13, 14 are formed in pairs at upper and lower positions on the lens setting portion 6 of the injector main body 2, and the upper wall portion inside of the insertion tube 4 opposed to the lens setting portion 6. The groves 13 and 14 constitute a suppressing portion for suppressing the lateral shake of the tip end part of the pushing member 5 when the pushing member 5 moves in the central axis direction of the injector main body 2. The term "lateral shake of the tip end part of the pushing member 5" refers to a situation that the tip end part of the rod portion 18 swings in the left-right direction when the pushing member 5 waiting behind the lens installing portion 6 is moved in the X1 direction by the rotation operation of the operation portion 3. When the tip end part of the pushing member 5 swings horizontally, the tip end part of the rod portion 18 cannot be stably brought into contact with a target position of the intraocular lens 7.

The groove 13 is formed on the lower side of the movement path of the rod portion 18, and the groove 14 is formed on the upper side of the movement path of the rod portion 18. Therefore, the groove 13 and the groove 14 are opposed to each other in a vertical direction interposing the movement path of the rod portion 18. In the following description, the lower groove 13 is referred to as a lower groove 13, and the upper groove 14 is referred to as an upper groove 14.

Figure 10A:
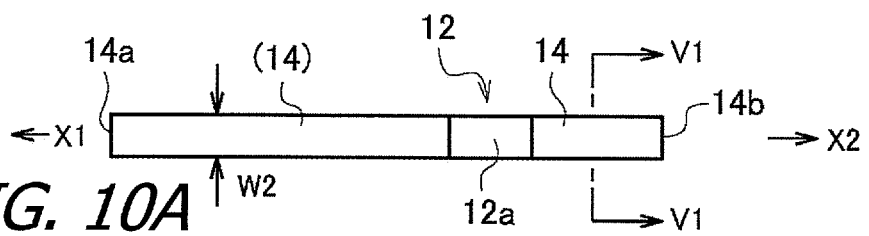
FIGS. 10A to 10D are views for explaining the structure of a lower groove and an upper groove, where
Figure 10B:
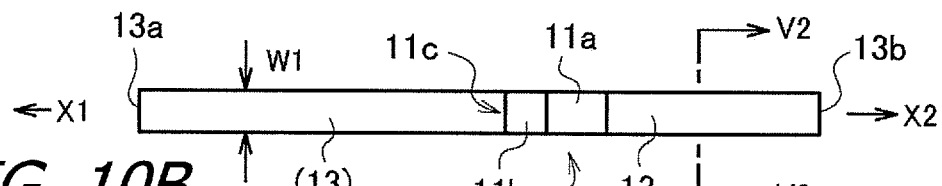
Figure 10C:
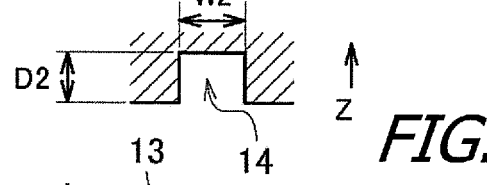
Figure 10D:
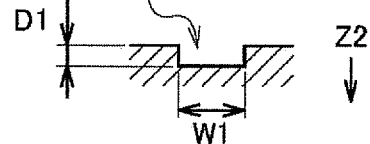

FIGS. 10A to 10D are views for explaining the structure of the lower groove and the upper groove, FIG. 10A is a schematic view when the upper groove is viewed from the position of the central axis of the injector main body, FIG. 10B is a schematic view when the lower groove is viewed from the position of the central axis of the injector main body, FIG. 10C is a view showing a sectional structure of the upper groove at the position V1-V1 of FIG. 10A, and FIG. 10D is a view showing a sectional structure of the lower groove at the position V2-V2 of FIG. 10B.

The lower groove 13 and the upper groove 14 are formed so as to be engaged with the tip end part of the rod portion 18 of the pushing member 5 in order to suppress the lateral shake of the tip end part of the pushing member 5. Specifically, the lower groove 13 is recessed downward and the upper groove 14 is recessed upward. Further, a width W1 of the lower groove 13 is set corresponding to a width of the tip end part of the rod portion 18, and a width W2 of the upper groove 14 is also set corresponding to a width dimension of the tip end part of the rod portion 18. FIG. 9 shows a state before the operation portion 3 of the intraocular lens injector 1 is rotated, namely, shows an initial state. In this initial state, the tip end part of the rod portion 18 receives a downward force. This downward force can be generated, for example, by elastically deforming the rod portion 18 itself so as to press the tip end part of the rod portion 18 downward. This point is the same in the first embodiment as well. Further, in the initial state, the lower side of the tip end part of the rod portion 18 is engaged with the lower groove 13.

In the central axis direction of the intraocular lens injector 1, a range S1 for forming the lower groove 13 is a range from a tip end 13a to a rear end 13b of the lower groove 13, and a range S2 for forming the upper groove 14 is a range from a tip end 14a to a rear end 14b of the upper groove 14. The lower guide slope 11 is included in the range S1 of the lower groove 13, and the upper guide slope 12 is included in the range S2 of the upper groove 14. The lower groove 13 and the upper groove 14 are formed linearly respectively along the central axis direction of the intraocular lens injector 1. The lower guide slope 11 is formed in the middle of the lower groove 13, and the upper guide slope 12 is formed in the middle of the upper groove 14.

The tip end 13a of the lower groove 13 is disposed at substantially the same position as the tip end 14a of the upper groove 14, and the rear end 13b of the lower groove 13 is disposed at a position displaced rearward from the rear end 14b of the upper groove 14. Therefore, the range S1 of the lower groove 13 is wider (longer) than the range S2 of the upper groove 14. Further, in the portion where the lower guide slope 11 is formed, the lower groove 13 is partly interrupted by the protrusion of the lower guide slope 11. The upper groove 14 is continuously formed in the middle of the range S2 without interruption. A depth D1 of the lower groove 13 is substantially uniform throughout the range S1. However, in the vicinity of the tip 13a of the lower groove 13, the depth D1 of the lower groove 13 gradually becomes shallow. A depth D2 of the upper groove 14 is deeper on the upstream side than the downstream side of the upper side guide slope 12. Further, in the portion where the upper guide slope 12 is formed, the depth D2 of the upper groove 14 is continuously changed in accordance with the inclination of the inclined portion 12a.

Next, an operation of the intraocular lens injector according to a second embodiment of the present invention will be described.

When the user rotates the operation portion 3, the pushing member 5 moves forward. At this time, the rod portion 18 of the pushing member 5 moves as shown in FIGS. 11A to 12B.

Figure 5C:
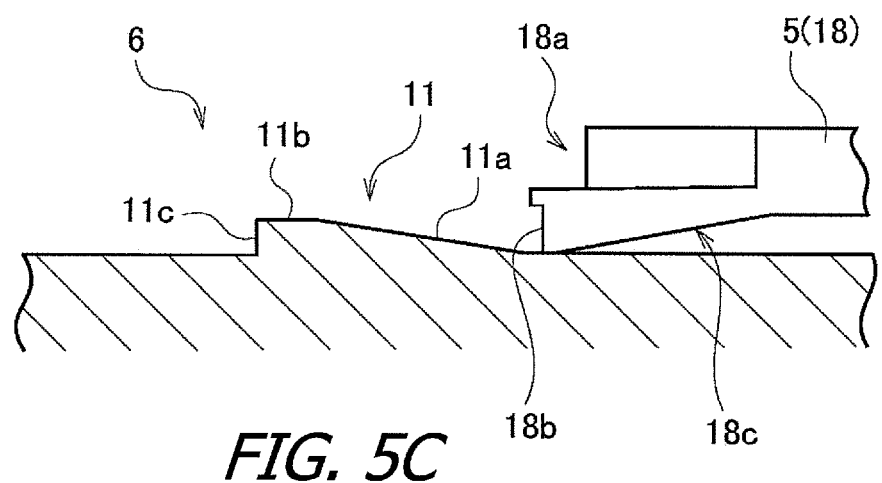
FIG. 5C is a partially enlarged view of FIG. 5B.
Figure 11A:
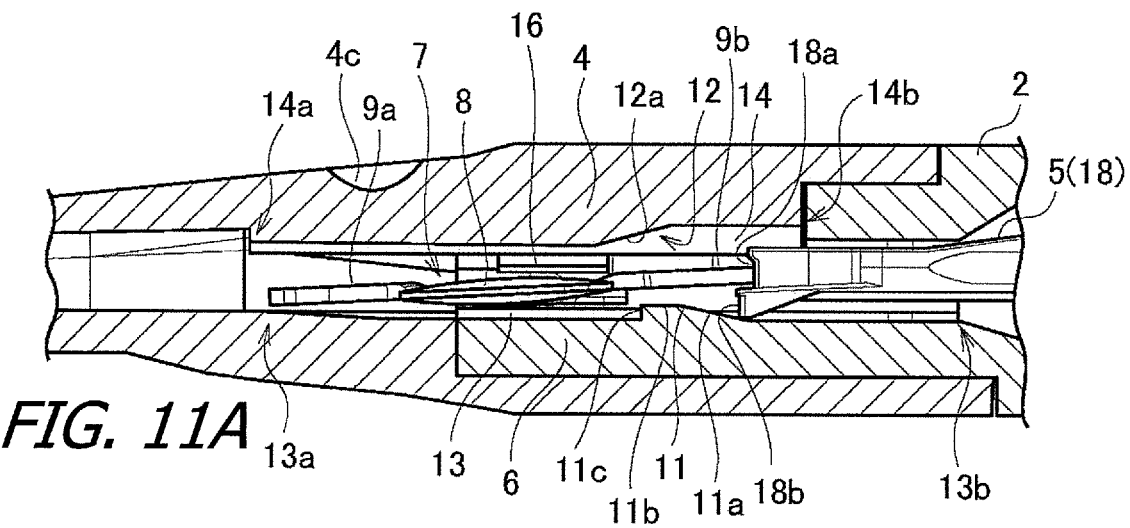
FIGS. 11A to 11C are views (part 1) for explaining an operation of the intraocular lens injector according to the second embodiment of the present invention.
Figure 12A:
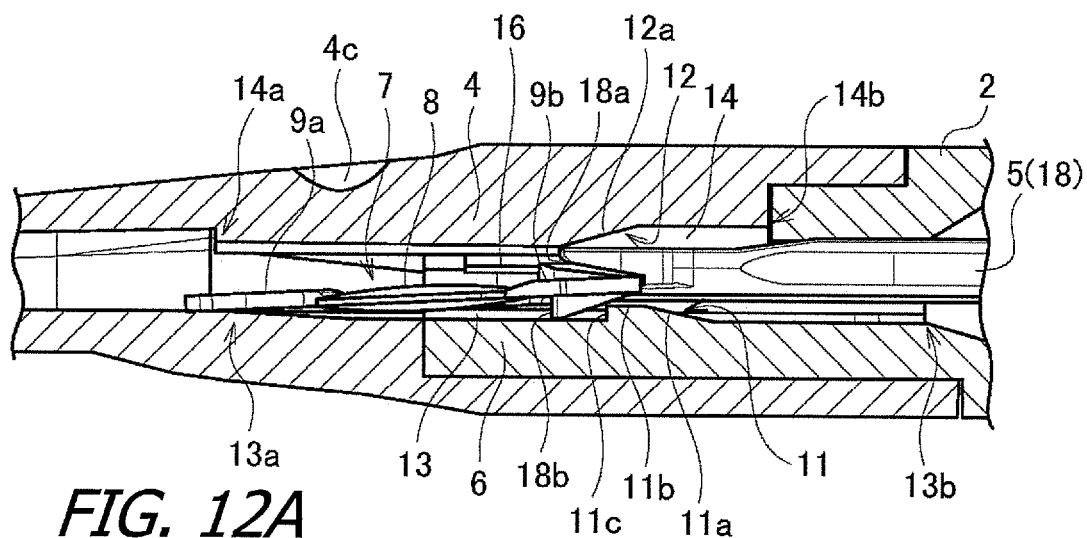
FIGS. 12A and 12B are views (part 2) for explaining the operation of the intraocular lens injector according to the second embodiment of the present invention.

FIG. 11A shows a stage in which the tip end part of the rod portion 18 of the pushing member 5 moves to a position in front of the lower guide slope 11, FIG. 8B shows a stage in which the tip end part of the rod portion 18 moves to the inclined portion 11a of the lower guide slope 11, and FIG. 5C shows a stage in which the tip end part of the rod portion 18 is moved to the top portion 11b of the lower guide slope 11. Further, FIG. 12A shows a stage in which the tip end part of the rod portion 18 moves forward of the lower guide slope 11, and FIG. 8B shows a stage in which the tip end part of the rod portion 18 moves forward of the upper guide slope 12.

First, in the process from the initial state of FIG. 9 to the state of FIG. 11A, the tip end part of the rod portion 18 moves forward while being engaged with the lower groove 13, and during this movement, the first contact portion 18a of the rod portion 18 comes into contact with the support portion 9b of the intraocular lens 7. Thereby, the tip end side of the support portion 9b is supported in a manner of riding onto the first contact portion 18a. Further, the tip end part of the rod portion 18 also engages with the upper groove 14 in the middle of the movement.

Figure 11B:
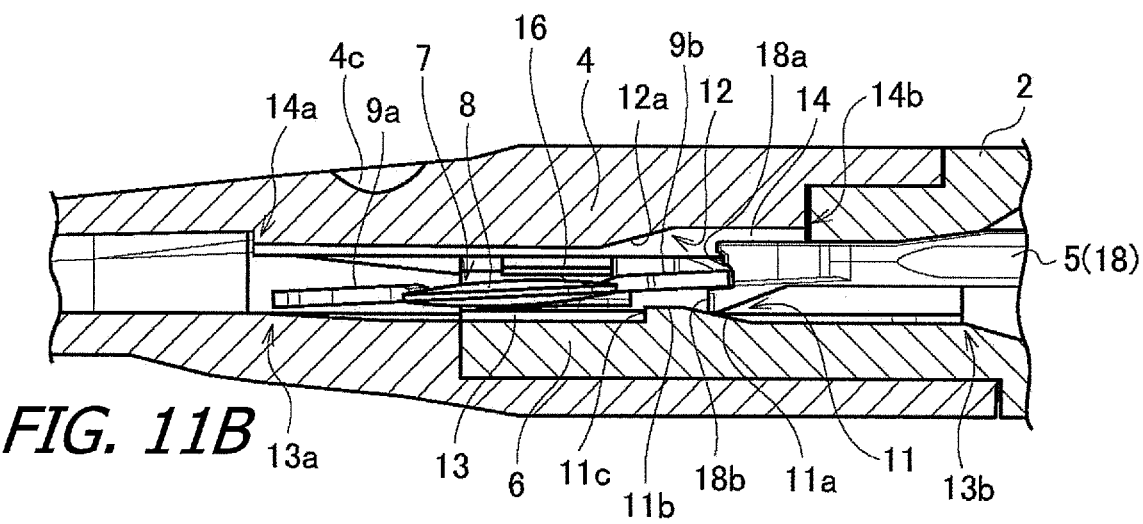

Next, in the process from the state of FIG. 11A to the state of FIG. 11B, the tip end part of the rod portion 18 moves while displacing upward along the inclined portion 11a of the lower guide slope 11. At this time, the tip end part of the rod portion 18 moves so as to push the support portion 9b while displacing upward by the elastic deformation of the rod portion 18 itself. Thereby, the support portion 9b is gradually bent. Further, the tip end side of the support portion 9b is gradually raised.

Figure 11C:
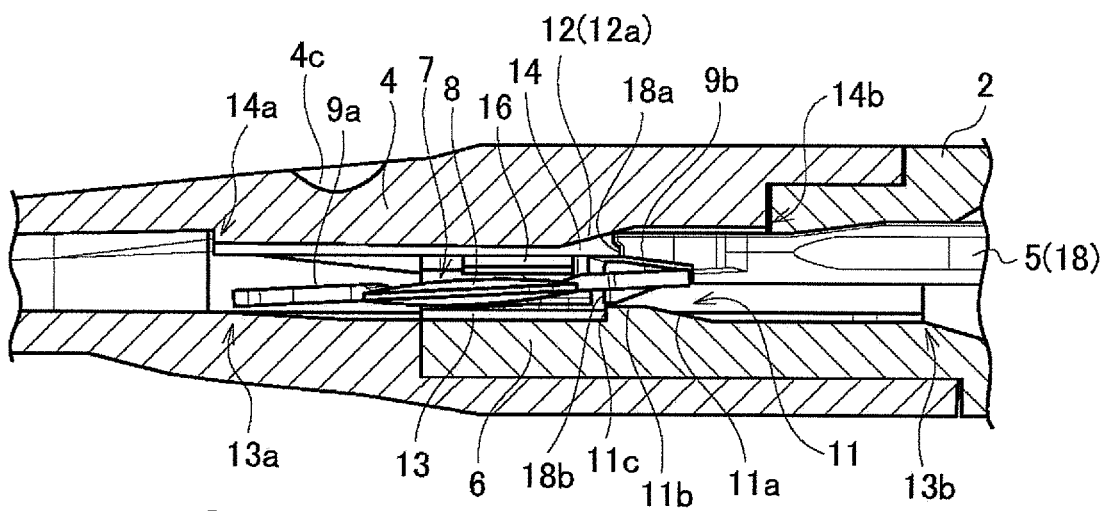

Next, in the process from the state of FIG. 11B to the state of FIG. 11C, the tip end part of the rod portion 18 reaches the top portion 11b while displacing upward along the inclined portion 11a of the lower guide slope 11, and thereafter moves along the top portion 11b. At that time, the tip end part of the rod portion 18 moves while being engaged with the upper groove 14. Further, the second contact portion 18b of the rod portion 18 comes into contact with the edge of the optical portion 8 in the middle of or immediately after passing through the top portion 11b.

Next, in the process from the state of FIG. 11C to the state of FIG. 12A, the tip end part of the rod portion 18 moves while being displaced downward along the inclined portion 12a of the upper guide slope 12. At this time, the tip end part of the rod portion 18 moves while being engaged with the upper groove 14, and passes through the lower guide slope 11, and thereafter is engaged with the lower groove 13 again, and returns to an original height position. Further, the tip end parts (18a, 18b) of the rod portion 18 push the entire intraocular lens 7 while being in contact with the support portion 9b and the optical portion 8. Therefore, the intraocular lens 7 further moves forward from the initial state.

Here, in the second embodiment, the guide slope 11 similar to that of the first embodiment is formed, and therefore even if the upper guide slope 12 is not formed, it is possible to displace the tip end part of the rod portion 18 downward by the same principle as in the first embodiment. However, when the rod portion 18 is easy to bend, a reaction force due to the elastic deformation of the rod portion 18 becomes weaker, and therefore there is a possibility that the operation of the rod portion 18 becomes unstable when the tip end part of the rod portion 18 rides onto the lower guide slope 11. Accordingly, in order to operate the rod portion 18 more stably, it is preferable to form the upper guide slope 12.

When the upper guide slope 12 is formed as in the second embodiment, the upper end of the tip end part of the rod portion 18 approaches or comes into contact with the inclined portion 12a of the upper guide slope 12, immediately after the tip end part of the rod portion 18 passes through the step portion 11c of the lower guide slope 11. Therefore, the tip end part of the rod portion 18 is forcibly displaced downward along the inclined portion 12a of the upper guide slope 12. Accordingly, the displacement operation of the rod portion 18 becomes more stable.

Figure 12B:
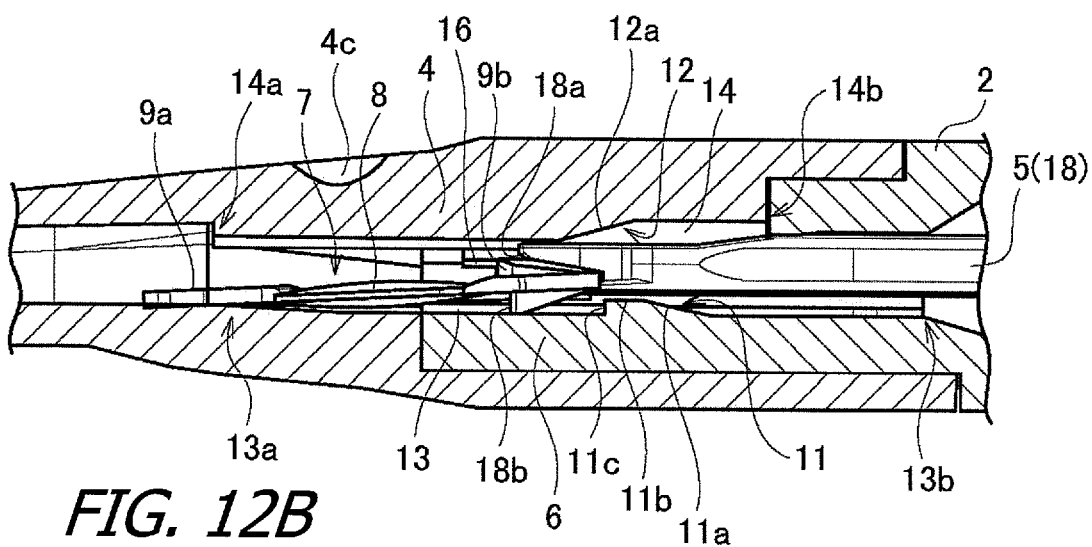

Next, in the process from the state of FIG. 12A to the state of FIG. 12B, the tip end part of the rod portion 18 moves while being engaged with both the lower groove 13 and the upper groove 14. At this time, the tip end parts (18a, 18b) of the rod portion 18 further push the entire intraocular lens 7 while coming into contact with the support portion 9b and the optical portion 8.

Thereafter, the tip end part of the rod portion 18 moves further forward while being engaged with both the lower groove 13 and the upper groove 14. At that time, the tip end part of the rod portion 18 disengages from the lower groove 13 at the stage of passing through the distal end 13a of the lower groove 13, and disengages from the upper groove 14 at the stage of passing through the tip end 14a of the upper groove 14. Therefore, the tip end part of the rod portion 18 moves while being engaged with both the lower groove 13 and the upper groove 14 except when it passes through the portion of the lower guide slope 11. Further, the tip end part of the rod portion 18 moves while being engaged with the upper groove 14 when it passes through the portion of the lower guide slope 11. Accordingly, the end portion of the rod portion 18 is continuously suppressed from the lateral shake due to the engagement with at least one of the grooves 13, 14 until the end of the passage through the ranges S1, S2 of the grooves 13, 14.

According to the second embodiment of the present invention, the following effects can be obtained in addition to the same effect as the first embodiment.

Namely, in the second embodiment of the present invention, the guide mechanism for guiding the movement of the pushing member 5 is constituted by the lower guide slope 11 and the upper guide slope 12. Therefore, it is possible to more stably perform the operation of vertically displacing the tip end part of the rod portion 18 of the pushing member 5.

Further, according to the second embodiment of the present invention, the lateral shake of the tip end part of the rod portion 18 is suppressed by the upper and lower grooves 13 and 14 when the tip end part of the rod portion 18 of the pushing member 5 is displaced in the vertical direction. Therefore, the tip end part of the rod portion 18 can be advanced straight. Accordingly, it is possible to bring the tip end part of the rod portion 18 into stable contact with the target position of the intraocular lens 7.

In the second embodiment, the lower groove 13 and the upper groove 14 are formed in order to suppress the lateral shake of the tip end part of the pushing member 5. However, a structure other than the groove may be adopted as long as it exhibits the same function.

Third Embodiment

A third embodiment of the present invention will be described hereafter.

Generally, the one-piece type intraocular lens 7 is made of a very soft material, and therefore when the support portion 9b is pushed in by the rod portion 18, there is a possibility that the shape of the support portion 9b is largely collapsed because the support portion 9b does not bend into a shape as expected by design. When such a phenomenon occurs, even if the support portion 9b is pushed by the rod portion 18, the tip end part of the support portion 9b can not be placed on the surface of the optical portion 8 as specified.

Therefore, in the third embodiment of the present invention, explanation will be given for the intraocular lens injector 1 suitable for handling the one-piece type intraocular lens 7 in which the entire intraocular lens 7 is made of a soft material. However, the intraocular lens injector 1 according to the third embodiment of the present invention can also be applied to a case of handling intraocular lenses other than the one-piece type.

In the third embodiment of the present invention, the structure of the lens setting portion 6 of the injector main body 2 is different, compared to the first embodiment described above.

The structure of the lens setting portion 6 will be described hereafter in detail with reference to FIG. 13.

A guide groove 21 is formed in the lens setting portion 6. The guide groove 21 constitutes a guide mechanism for guiding the movement of the tip end part of the pushing member 5, when the pushing member 5 moves in the central axis direction of the injector main body 2. The guide groove 21 is formed in such a manner that the upper surface of the lens setting portion 6 is recessed in a concave shape in front of a region where the optical portion 8 is disposed in the lens setting portion 6. The guide groove 21 is curved with respect to the central axis J when the lens setting portion 6 is viewed from above. Specifically, in the moving direction of the pushing member 5, the upstream side (the right side in the figure) of the guide groove 21 curves in the right direction Y1 so as to be away from the position of the central axis J, and the downstream side (the left side in the figure) of the guide groove 21 is curved in the left direction Y2 so as to approach the position of the central axis J.

The tip end part of the rod portion 18 is engaged with the guide groove 21. The tip end part of the rod portion 18 is configured to move along the guide groove 21 while being engaged with the guide groove 21. Further, when the tip end part of the rod portion 18 moves along the guide groove 21, a starting end portion 21a of the guide groove 21 which is a starting side of the movement is located on the central axis J in the left-right direction, and an end point 21b of the guide groove 21 on the opposite side is also located on the central axis J in the left-right direction.

In contrast, the tip end part of the support portion 9b is disposed so as to block a movement path of the rod portion 18 moving along the guide groove 21, when the intraocular lens 7 is set on the lens setting portion 6. Further, the tip end part of the support portion 9b is disposed at an middle point 21c in a longitudinal direction of the guide groove 21. In the middle point 21c of the guide groove 21, a curved direction of the guide groove 21 is switched from the right direction Y1 to the left direction Y2, and the tip end part of the support portion 9b is disposed in this portion.

When the intraocular lens 7 is set on the lens setting portion 6 having the above structure and the pushing member 5 is moved by the rotating operation of the operation portion 3, the tip end part of the rod portion 18 moves as follows by being guided by the guide groove 21.

Figure 13:
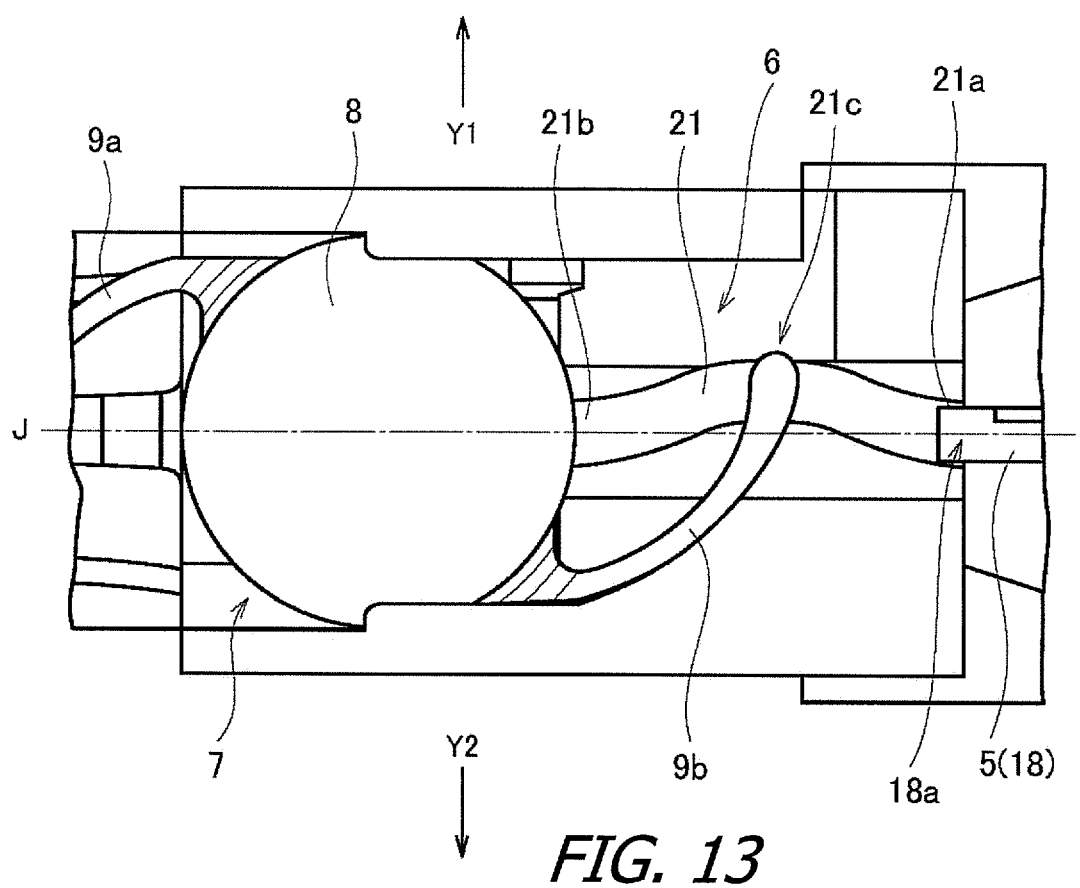
FIG. 13 is an enlarged plan view of the essential structure of the intraocular lens injector according to a third embodiment of the present invention.
Figure 14A:
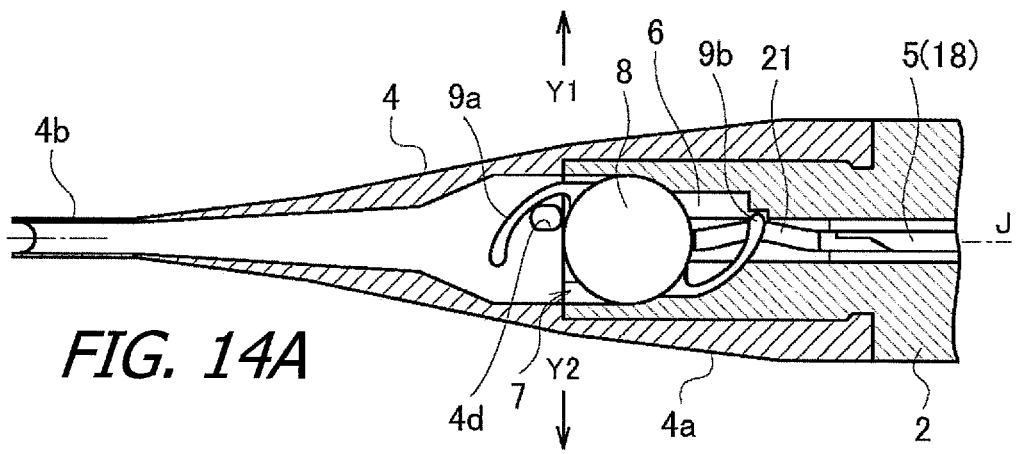
FIGS. 14A to 14C are plan sectional views (part 1) showing time-sequentially a state of pushing out the intraocular lens in the intraocular lens injector, using a pushing member according to the third embodiment of the present invention.

First, as shown in FIG. 14A, the tip end part of the rod portion 18 starts to move from a starting point 21a of the guide groove 21 located on the central axis J (see FIG. 13).

Figure 14B:
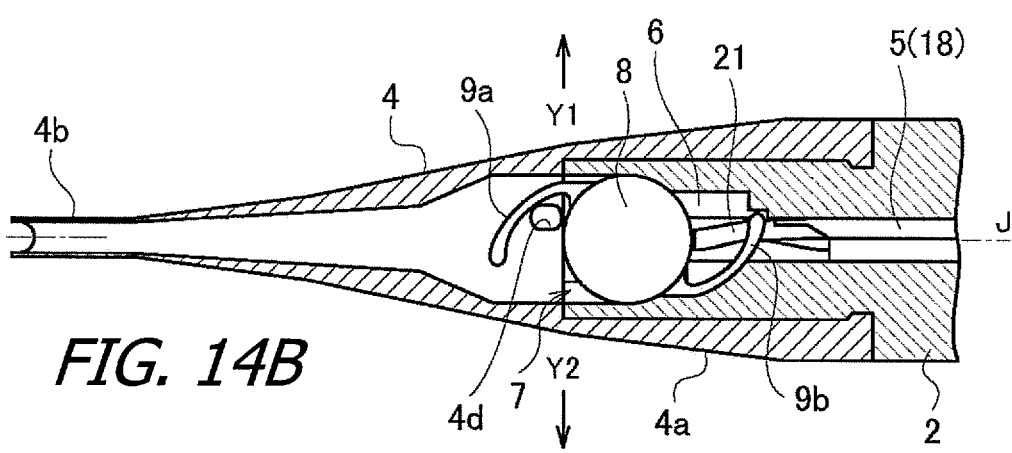

Next, as shown in FIG. 14B, the tip end part of the rod portion 18 moves from the starting point 21a to the middle point 21c of the guide groove 21 (see FIG. 13) along the guide groove 21. At this time, the tip end part of the rod portion 18 moves (advances) while displacing to the right direction Y1, due to the elastic deformation of the rod portion 18 itself. Further, the tip end part of the rod portion 18 comes into contact with the tip end part of the support portion 9b at a position where it reaches the middle point 21c of the guide groove 21 (in other words, at a position deviated from the position of the central axis J in the right direction Y1). Specifically, the first contact portion 18a formed at the tip end part of the rod portion 18 comes into contact with the tip end part of the support portion 9b. Thereby, the tip end part of the support portion 9b is supported in a manner of riding onto the first contact portion 18a.

Figure 14C:
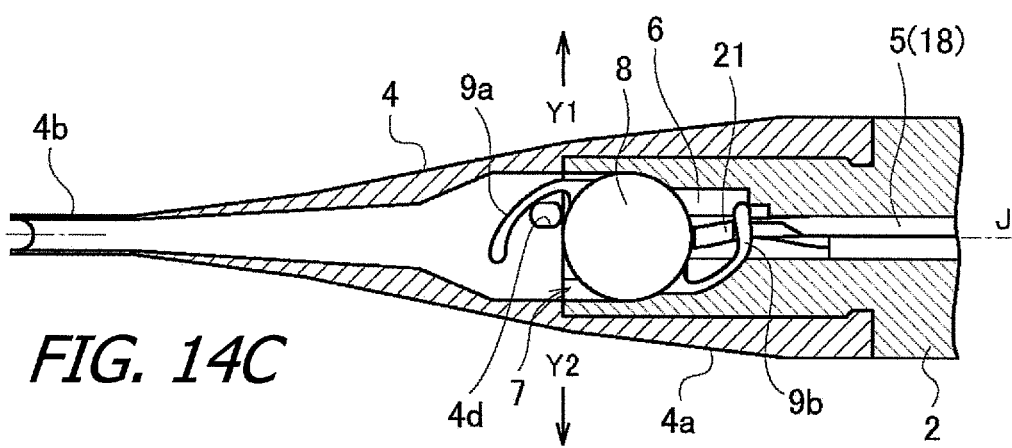
Figure 15A:
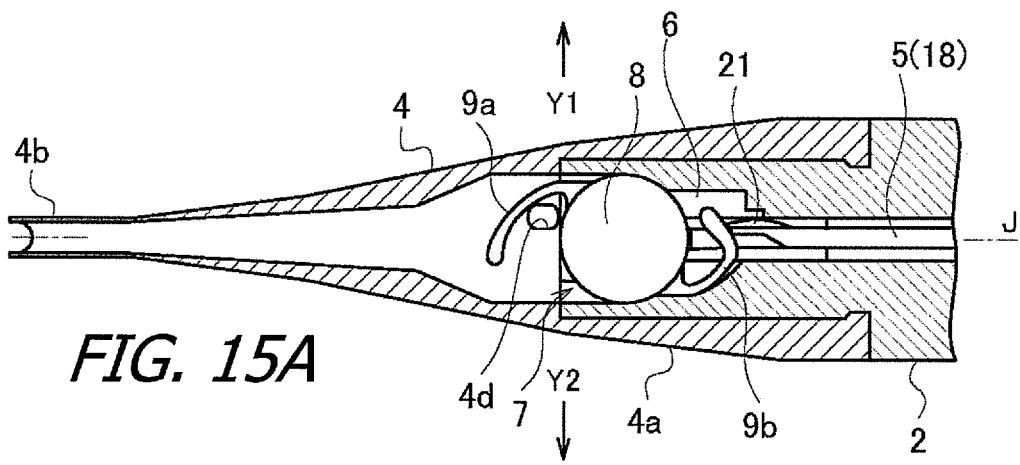
FIGS. 15A to 15C are plan sectional views (part 2) showing time-sequentially the state of pushing out the intraocular lens in the intraocular lens injector using the pushing member according to the third embodiment of the present invention.

Next, as shown in FIG. 14C, the tip end part of the rod portion 18 pushes the support portion 9b while moving along the guide groove 21. At this time, as shown in FIG. 15A, the support portion 9b is gradually bent by the forward movement of the rod portion 18. Further, the tip end part of the rod portion 18 moves (forwards) while displacing in the left direction Y2 in accordance with the curve of the guide groove 21.

Figure 15B:
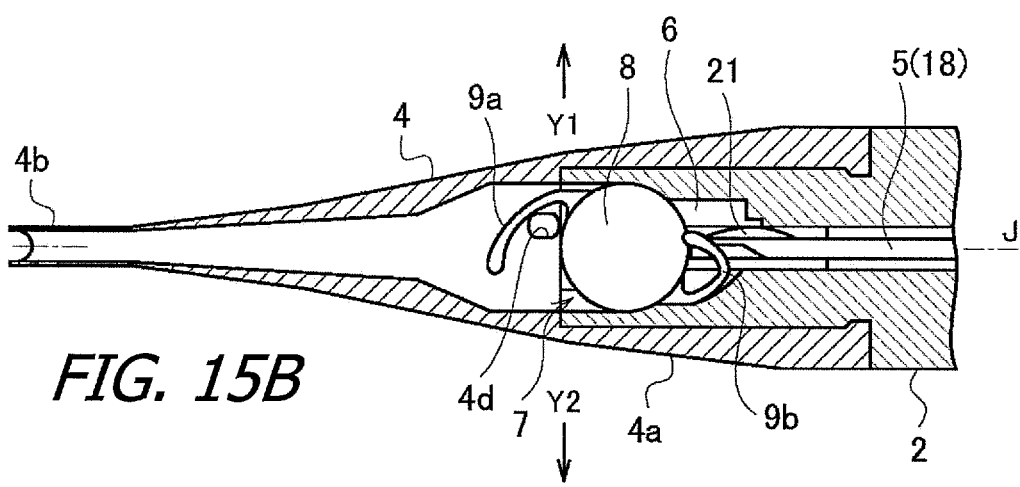

Next, as shown in FIG. 15B, the tip end part of the rod portion 18 comes into contact with the optical portion 8 when it reaches the end point 21b (see FIG. 13) of the guide groove 21 located on the central axis J. At this time, the tip end part of the rod portion 18 comes into contact with the optical portion 8 at the position of the central axis J passing through substantially the center of the optical portion 8. Specifically, the second contact portion 18b formed at the tip end part of the rod portion 18 comes into contact with the edge of the optical portion 8. Further, the support portion 9b is further bent by the forward movement of the rod portion 18 along the guide groove 21. Specifically, the support portion 9b as a whole is bent toward the optical portion 8 so as to form a substantially U-shape.

Figure 15C:
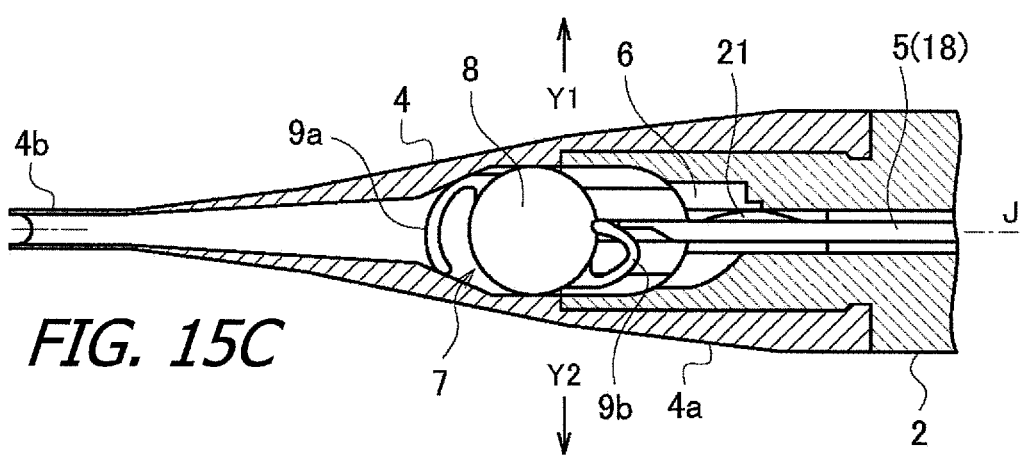

Next, as shown in FIG. 15C, the tip end part of the rod portion 18 pushes the entire intraocular lens 7 while being in contact with the support portion 9b and the optical portion 8. In this stage, the tip end part of the rod portion 18 has passed through the guide groove 21. Therefore, the tip end part of the rod portion 18 moves straight along the central axis J. Hereinafter, the description is omitted since it is the same as the first embodiment described above.

In the third embodiment of the present invention, when the pushing member 5 moves in the central axis direction of the injector main body 2, the tip end part of the rod portion 18 is guided by the guide mechanism so as to be displaced in a direction crossing the central axis of the injector main body 2 (in the left-right direction in this embodiment). With this structure, it is possible to bend the support portion 9b into a shape as expected, when the tip end part of the rod portion 18 is sequentially brought into contact with the support portion 9b and the optical portion 8 by the movement of the pushing member 5. This point will be described in more detail.

First, when it is assumed that the tip end part of the rod portion 18 is moved straight along the central axis J without being displaced (curved) in the left-right direction, the position where the tip end part of the rod portion 18 comes into contact with the support portion 9b is positioned closer to the middle point in the longitudinal direction of the support portion 9b, as compared with the third embodiment. When the tip end part of the rod portion 18 is brought into contact with the support portion 9b at such a position, a risk that the tip end side of the support portion 9b is bent in a direction different from an expected direction by design (typically the opposite direction) is increased when the support portion 9b is pushed in by the tip end part of the rod portion 18. As a result, there is a possibility that the tip end part of the support portion 9b cannot be placed on the surface of the optical portion 8 as specified.

In contrast, in the third embodiment, first, the tip end part of the rod portion 18 is brought into contact with the tip end part of the support portion 9b at a position deviated in the right direction Y1 from the position of the central axis J, and thereafter the tip end part of the rod portion 18 is displaced in the left direction Y2 and is brought into contact with the optical portion 8 at the position of the central axis J. Therefore, the tip end side of the support portion 9b can be bent in the shape as expected by design when the support portion 9b is pushed in by the tip end part of the rod portion 18. Accordingly, the support portion 9b can be bent into a shape as expected. As a result, it is possible to reliably place the tip end part of the support portion 9b on the surface of the optical portion 8.

Further, according to the third embodiment of the present invention, by forming the guide groove 21 in the injector main body 2 and displacing the tip end part of the rod portion 18 in the left-right direction along the guide groove 21, it is possible to suppress the shape collapse of the support portion 9b. Thereby, it is possible to bend the tip end side of the support portion 9b into a shape as expected and place the tip end part of the support portion 9b on the surface of the optical portion 8.

Fourth Embodiment

A fourth embodiment of the present invention will be described hereafter.

In the fourth embodiment of the present invention, compared with the abovementioned first embodiment, the structure of the injector main body 2 and the injection tube 4 are different, as compared to the abovementioned first embodiment. Here, first, a comparative embodiment of the present invention will be described, and thereafter the fourth embodiment of the present invention will be described.

Figure 16A:
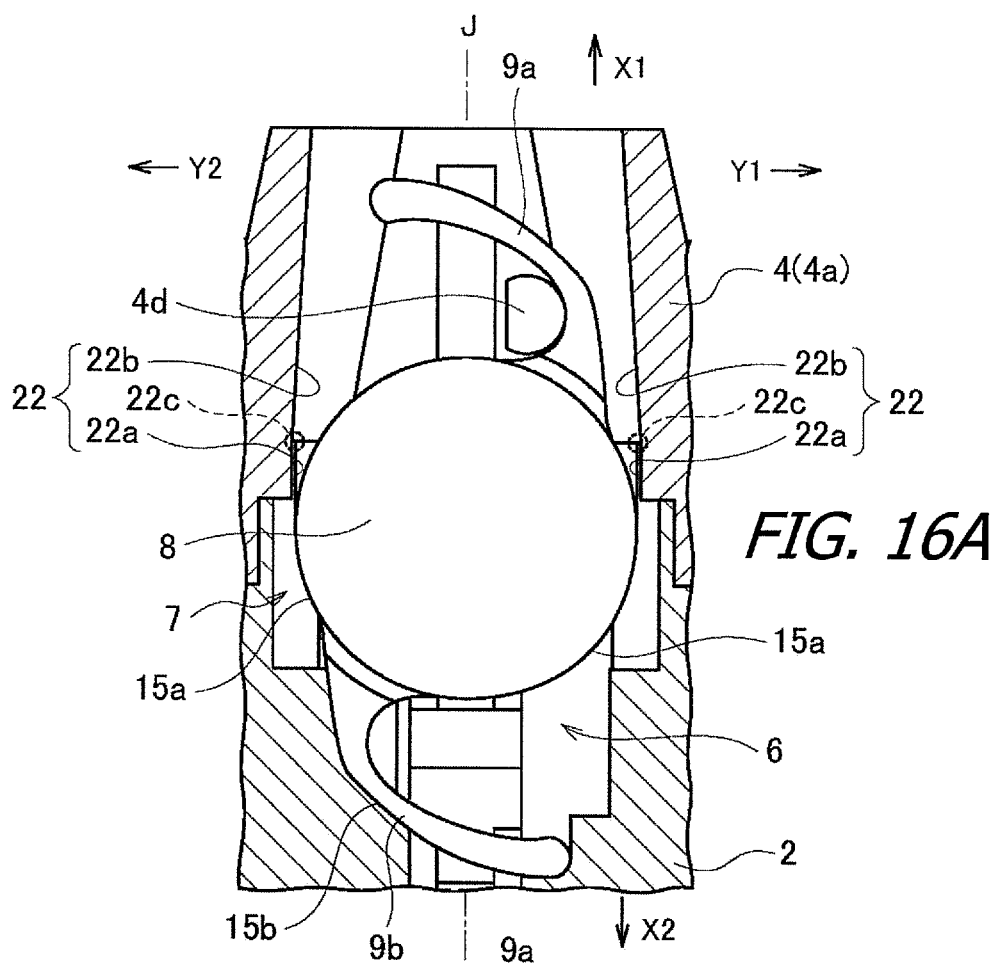
FIGS. 16A and 16B show an internal structure of a joint portion between the injector main body and an injection tube as an essential part of the intraocular lens injector according to a comparative embodiment of the present invention, where
Figure 16B:
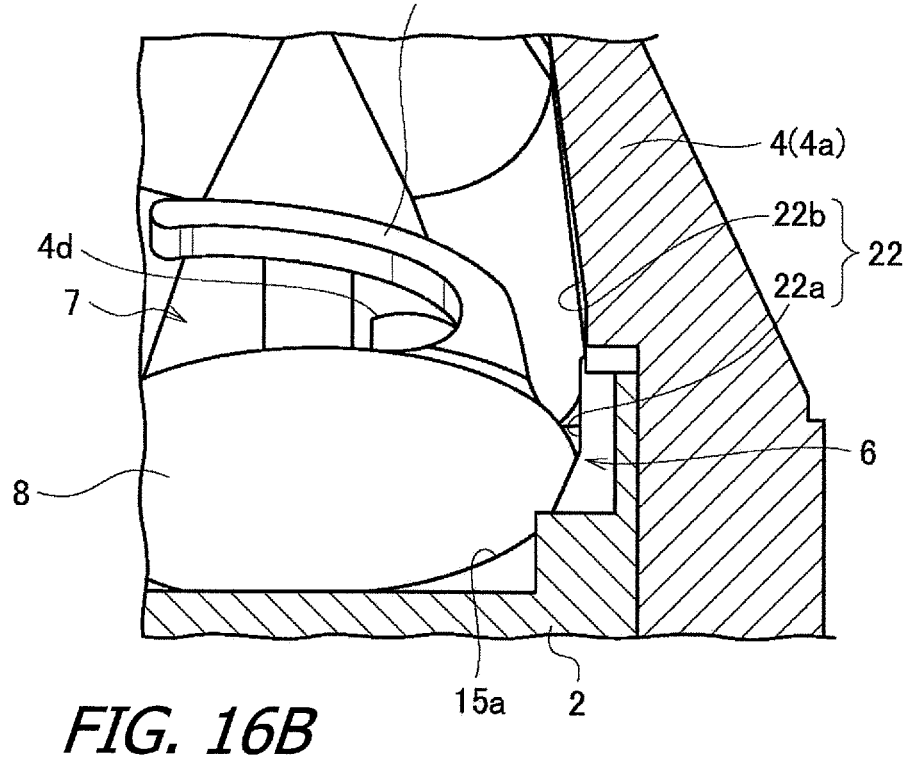

FIGS. 16A and 16B show an internal structure of a joint portion between the injector main body and an injection tube as an essential part of the intraocular lens injector according to a comparative embodiment of the present invention, where FIG. 16A is a view of the internal structure of the joint portion viewed from above, and FIG. 16B is a perspective view of the internal structure of the joint portion viewed from backside.

Edge portions 15a, 15b for positioning the intraocular lens 7 placed thereon are formed in the lens setting portion 6 of the injector main body 2. The edge portion 15a is formed in a shape conforming to an outer shape of the optical portion 8, and the edge portion 15b is formed in a shape conforming to an outer shape of the support portion 9b. A step is provided on each of the edge portions 15a and 15b, and positioning of the intraocular lens 7 can be performed by using this step difference. Namely, in the lens setting portion 6, the optical portion 8 is disposed along the edge portion 15a, and the support portion 9b is disposed along the edge portion 15b, to thereby determine a setting position (hereinafter referred to as "an initial position") of the intraocular lens 7 in an initial state. A position of the optical portion 8 at the time of setting the intraocular lens 7 at the initial position, is a position where the optical portion 8 starts moving when the intraocular lens 7 is pushed out by the pushing member 5. Therefore, the movement start position of the optical portion 8 in the lens setting portion 6 is set using the edge portion 15a.

A pair of right and left side wall guides 22, 22 are formed from the lens setting portion 6 to the inside of the injection tube 4 in the central axis direction of the intraocular lens injector 1. The pair of side wall guides 22 have guide surfaces 22a and 22b respectively that regulate the position in the right and left direction of the optical portion 8 by bringing the optical portion 8 close to or in contact with the left and right edges of the optical portion 8. One guide surface 22a is formed in the lens setting portion 6 and the other guide surface 22b is formed inside of the injection tube 4. In the following description, one guide surface 22a is referred to as a first guide surface 22a, and the other guide surface 22b is referred to as a second guide surface 22b.

The first guide surface 22a is formed on the lens setting portion 6 so as to be smoothly connected to the edge portion 15a. The first guide surface 22a is formed straight along the central axis J of the intraocular lens injector 1. The second guide surface 22b is formed on the side wall portion of the injection tube 4 so as to smoothly connect to the first guide surface 22a. The second guide surface 22b has an inclination with respect to the central axis J of the intraocular lens injector 1. Specifically, the second guide surface 22b is gradually inclined inward (toward the central axis J of the intraocular lens injector 1) from a joint portion 22c between the first guide surface 22a and the second guide surface 22b. Thereby, a distance in the left-right direction of the pair of side wall guides 22, 22 is as follows. First, in the portion where the first guide surface 22a is formed, the distance is equal to or slightly larger than an outer diameter of the optical portion 8. In contrast, in the portion where the second guide surface 22b is formed, the diameter is gradually decreased from the joint portion 22c with the first guide surface 22a toward the nozzle portion 4b (FIG. 1) of the injection tube 4.

Figures 17A, 17B:
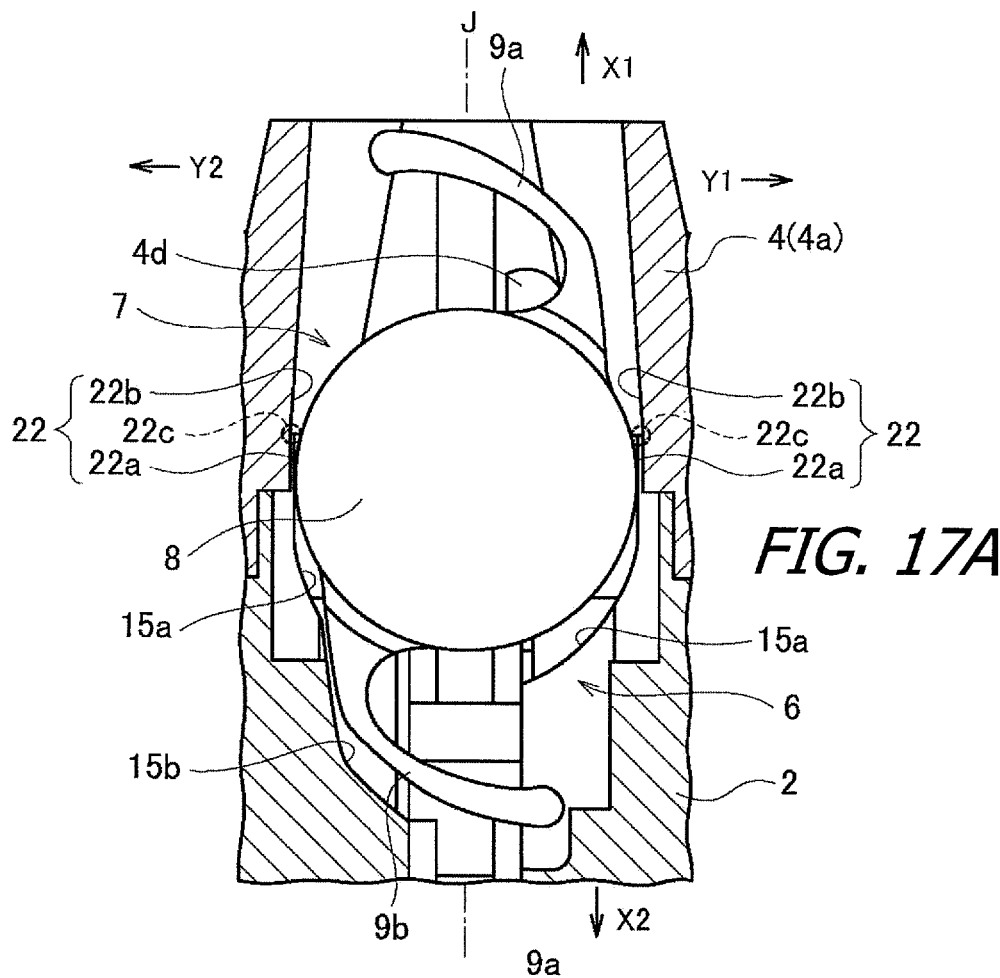
FIGS. 17(A) and 17(B) are views showing a state of the movement of the intraocular lens in an intraocular lens injector according to a comparative embodiment of the present invention.

In the comparative embodiment of the present invention, when the intraocular lens 7 set on the lens setting portion 6, is pushed out by the rod portion 18 of the pushing member 5, the intraocular lens 7 starts moving from the initial position. At this time, as shown in FIGS. 17A and 17B, the optical portion 8 moves forward (in the X1 direction) while being guided by the left and right first guide surfaces 22a. Next, the left and right edges of the optical portion 8 reach the joint portion 22c between the first guide surface 22a and the second guide surface 22b. In this joint portion 22c, the first guide surface 22a and the second guide surface 22b are smoothly connected. Therefore, the optical portion 8 moves forward without being caught by the joint portion 22c.

In the comparative embodiment, the second guide surface 22b is slightly outwardly disposed as compared with the first guide surface 22a so that the optical portion 8 is not caught by the joint portion 22c. Further, in FIGS. 17A and 17B, in order to easily understand how much the intraocular lens 7 has moved from the initial position shown in FIGS. 16A and 16B, the shape of the rear support portion 9b is shown in the same manner as in FIGS. 16A and 16B. However, actually the support portion 9b is pushed by the rod portion 18 and set in a bent state.

Next, the optical portion 8 moves further forward while being guided by the left and right second guide surfaces 22b. In this case, the distance between the left and right second guide surfaces 22b is gradually decreased toward the front, and accordingly, the space inside of the injection tube 4 is also gradually narrowed. Therefore, when the intraocular lens 7 is pushed out by the rod portion 18, the optical portion 8 is gradually bent while being guided by the left and right second guide surfaces 22b, and ultimately it is rounded small and folded.

Regarding the comparative embodiment described above, the present inventor has newly found out that there are further points to be improved.

First, in the comparative embodiment, the first guide surface 22a and the second guide surface 22b of each side wall guide 22 are smoothly connected. Therefore, the optical portion 8 of the intraocular lens 7 moves along the first guide surface 22a and the second guide surface 22b without stopping at the joint portion 22c. In such a case, depending on the physical characteristics of the intraocular lens 7, there is a possibility that the following troubles occurs.

The pair of support portions 9a, 9b have appropriate flexural rigidity to support the optical portion 8 in the eye. Therefore, depending on the intensity of the flexural rigidity of each of the support portions 9a, 9b, there is a possibility that the optical portion 8 starts to move in a state in which the bending deformation of the support portion 9b is insufficient, namely, at a timing earlier than expected when the support portion 9b is pushed in by the first contact portion 18a of the rod portion 18. In such a case, when the first guide surface 22a and the second guide surface 22b are smoothly connected as in the comparative embodiment, there is a possibility that the optical portion 8 is pushed forward with no riding of the tip end part of the support portion 9b onto the surface of the optical portion 8.

Further, when the optical portion 8 starts to move in a state in which the bending deformation of the support portion 9b is insufficient as described above, the tip end part of the support portion 9b is easily caught on the edge of the optical portion 8. The reason is as follows. A pair of right and left recessed grooves for limiting a vertical displacement amount of the optical portion 8 is formed in the lens setting portion 6. Then in the initial state, the left and right outer peripheral parts of the optical portion 8 are disposed in the corresponding recessed grooves, thereby restricting the movement of the optical portion 8 in the vertical direction. However, when the optical portion 8 starts to move in a state in which the bending deformation of the support section 9b is insufficient, there is a possibility that the outer peripheral part of the optical portion 8 is disengaged from the recessed groove before the tip end part of the support portion 9b rides onto the surface of the optical portion 8. Therefore, the restriction by the recessed groove is canceled and the optical portion 8 is displaced upward so that the tip end part of the support portion 9b is easily caught on the edge of the optical portion 8. As a measure against this situation, it is conceivable to lengthen the length of the recessed groove so that the outer peripheral part of the optical portion 8 is not disengaged from the recessed groove. However, by adopting this measure, when the optical portion 8 starts to bend due to contact with the second guide surface 22b, there is a possibility that the outer peripheral part of the optical portion 8 is caught on the recessed groove and the curved deformation of the optical portion 8 is inhibited. Therefore, there is a limit in lengthening the length of the recessed groove.

Figure 18A:
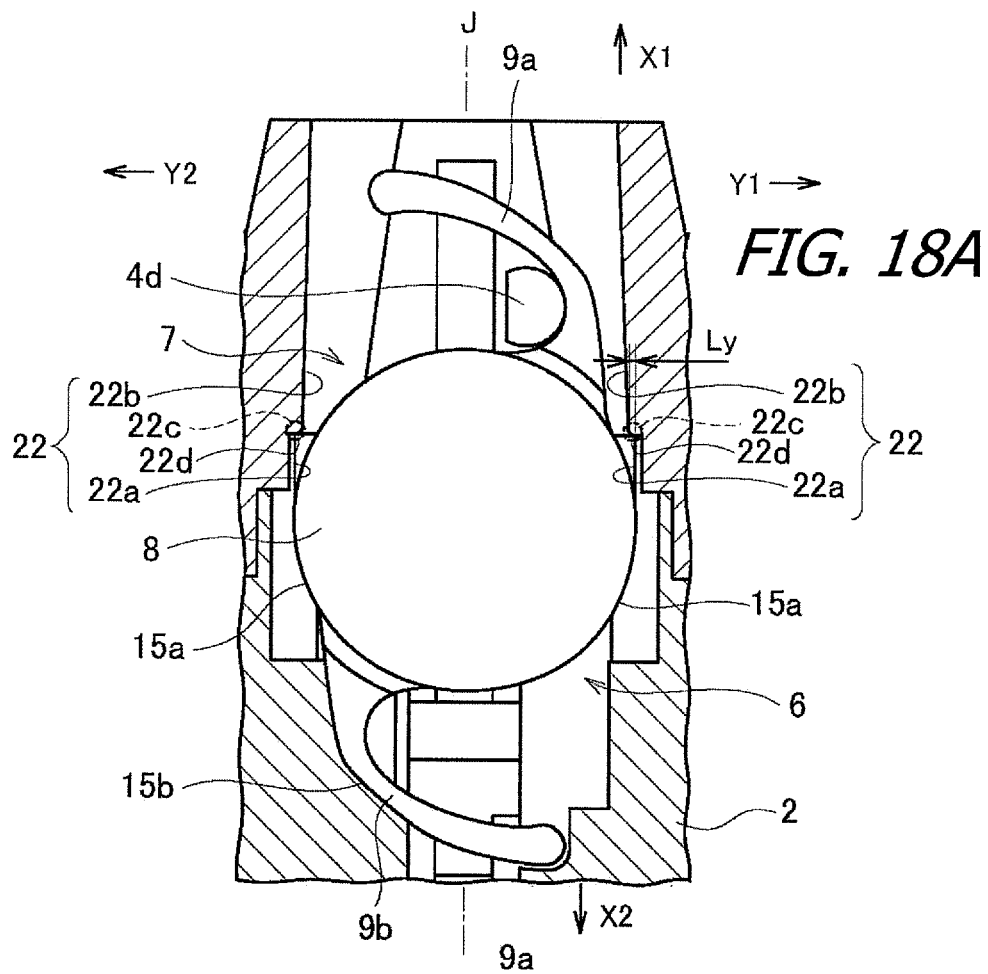
FIGS. 18A and 18B the internal structure of the joint portion between the injector main body and the injection tube as the essential part of the intraocular lens injector according to a fourth embodiment of the present invention, where
Figure 18B:
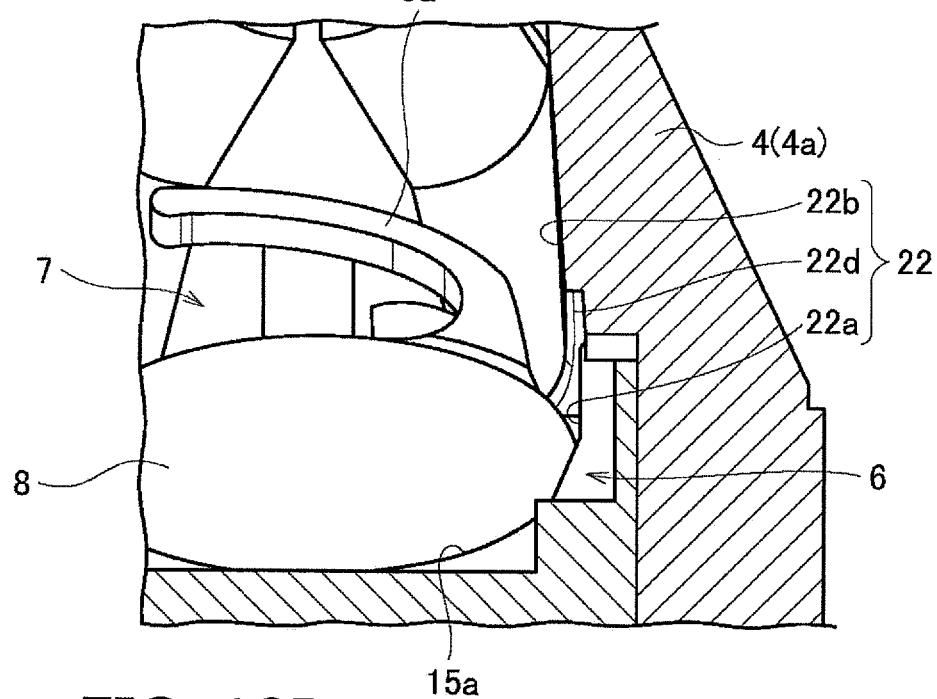

FIGS. 18A and 18B show the internal structure of the joint portion between the injector main body and the injection tube as the essential part of the intraocular lens injector according to a fourth embodiment of the present invention, FIG. 18A is a view of the internal structure of the joint portion viewed from above, and FIG. 18B is a perspective view of the internal structure of the joint portion viewed from the backside.

The fourth embodiment is intended to solve the problem which may occur in the above comparative embodiment. The difference between the fourth embodiment and the comparative embodiment lies in the structure of the pair of side wall guides 22, 22. Specifically, in the above comparative embodiment, the first guide surface 22a and the second guide surface 22b of each side wall guide 22 are smoothly connected. However, in the fourth embodiment, the first guide surface 22a and the second guide surface 22b are not connected smoothly but the protrusion 22d is formed on the joint portion 22c.

The protrusion 22d temporarily stops the optical portion 8 of the intraocular lens 7 pushed out by the pushing member 5. The protrusion 22d is formed at the joint portion 22c so that the second guide surface 22b protrudes inward from the first guide surface 22a (a side close to the central axis J of the intraocular lens injector 1) by a predetermined dimension Ly. Thereby, the distance between the left and right side wall guides 22, 22 is shorter than the diameter of the optical portion 8 due to the protrusion of the protrusion 22d. Therefore, when the intraocular lens 7 set at the initial position of the lens setting portion 6 is pushed out by the pushing member 5, the left and right edges of the optical portion 8 are caught on the corresponding protrusion 22d.

The protruding dimension Ly of the protrusion 22d corresponds to the amount of positional deviation in the left-right direction between the first guide surface 22a and the second guide surface 22b at the joint portion 22c, and it is preferably 0.1 mm or more and 0.5 mm or less. Since the protrusion 22d exists on both the left and right sides, for example, when the protruding dimension of the protrusion 22d is set to 0.2 mm, the distance between the left and right side wall guides 22 and 22 is shortened to 0.4 mm in total (0.2 mm on each side).

The protrusion 22d is disposed so that when the optical portion 8 is disposed at the movement start position, it does not contact the optical portion 8, and when the optical portion 8 moves from the movement start position by a predetermined amount M (see FIG. 19A), it comes into contact with the optical portion 8. The predetermined amount M is preferably 0.5 mm or more and 1.0 mm or less, and more preferably 0.6 mm or more and 0.8 mm or less. The predetermined amount M is set to be shorter than a moving distance of the optical portion 8 until the outer peripheral part of the optical portion 8 is disengaged from the left and right recessed grooves. Thereby, the optical portion 8 can be brought into contact with the protrusion 22*d* before the outer peripheral part of the optical portion 8 is disengaged from the recessed groove.

The distance between the left and right side wall guides 22, 22 is as follows. First, in the portion where the first guide surface 22*a* is formed, the above distance is the same as or slightly larger than the outer diameter of the optical portion 8 in the same manner as in the abovementioned comparative embodiment. In contrast, in the portion where the second guide surface 22*b* is formed, the above distance is gradually decreased from the protrusion 22*d* formed in the connecting portion 22*c* toward the nozzle portion 4*b* of the injection tube 4.

Figure 19A:
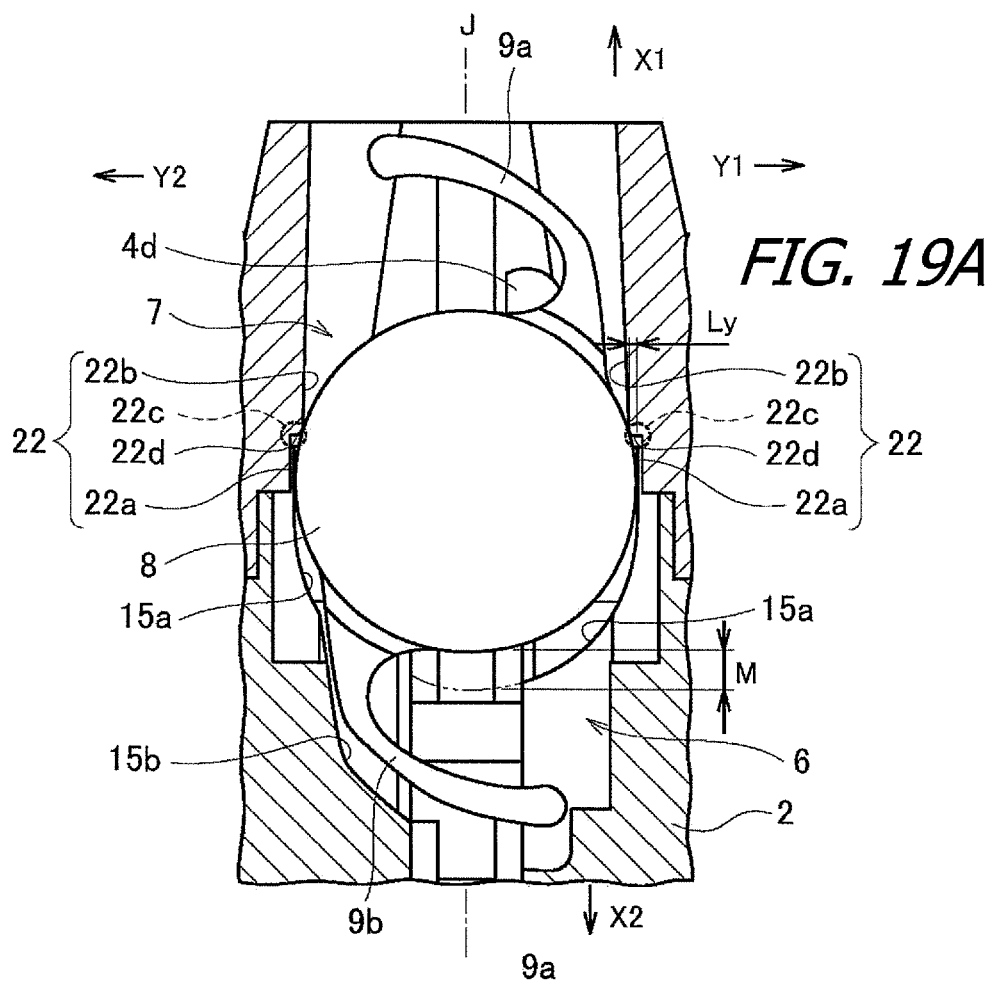
FIGS. 19A and 19B are views showing a state of the movement of the intraocular lens in an intraocular lens injector according to a fourth embodiment of the present invention.
Figure 19B:
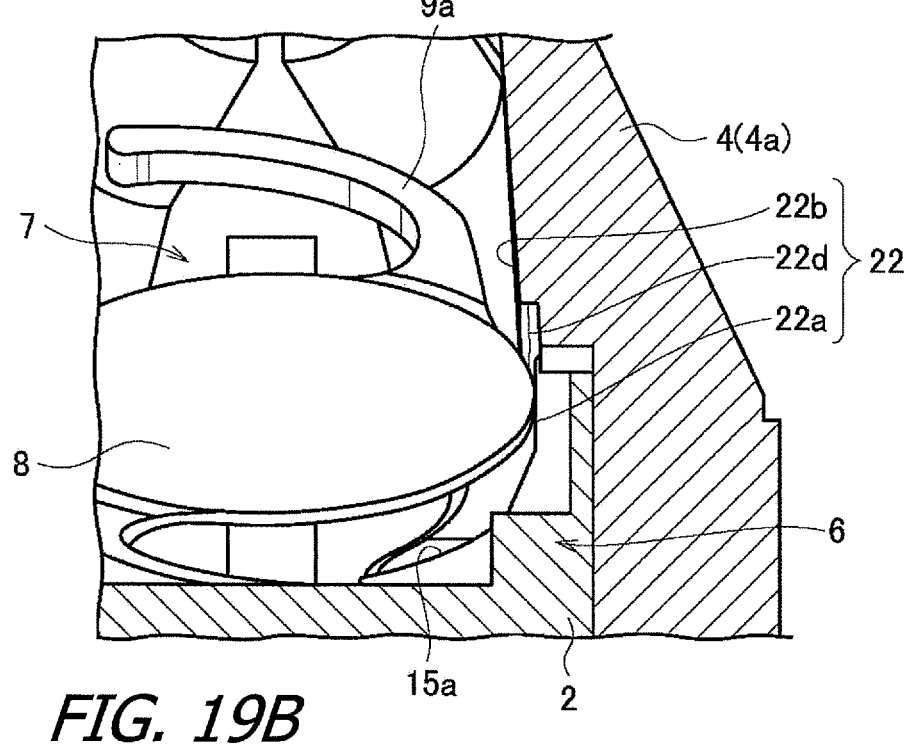

In the fourth embodiment of the present invention, when the intraocular lens 7 set on the lens setting portion 6 is pushed forward by the rod portion 18 of the pushing member 5, the intraocular lens 7 starts moving from its initial position. At this time, the optical portion 8 moves forward (in the X1 direction) while being guided by the left and right first guide surfaces 22*a*. Next, the left and right edges of the optical portion 8 reach the joint portion 22*c* between the first guide surface 22*a* and the second guide surface 22*b*. The protrusion 22*d* is formed on this joint portion 22*c*. Therefore, as shown in FIGS. 19A and 19B, the left and right edges of the optical portion 8 come into contact with and hooked on the corresponding protrusion 22*d* respectively, and the optical portion 8 is temporarily stopped by this hooking.

Accordingly, even when the optical portion 8 starts to move in a state in which the bending deformation of the support portion 9*b* is insufficient, the support portion 9*b* can be sufficiently bent at the tip end part of the rod portion 18 while the optical portion 8 is temporarily stopped so that the tip end part of the support portion 9*b* can be placed on the surface of the optical portion 8. Further, by temporarily stopping the optical portion 8 before the left and right outer peripheral parts of the optical portion 8 are disengaged from the recessed groove, the tip end part of the rod portion 18 can be brought into contact with the edge of the optical portion 8, while limiting the amount of displacement in the vertical direction (in particular, upward direction) of the optical section 8 by the recessed groove. Therefore, the tip end part of the support portion 9*b* can be placed on the surface of the optical portion 8 without being hooked on the edge of the optical portion 8.

When the tip end part of the rod portion 18 comes into contact with the edge of the optical portion 8 while the optical portion 8 is temporarily stopped as described above, thereafter, the optical portion 8 is forcibly pushed out by the rod portion 18. Therefore, the hooking of the optical portion 8 on the pair of protrusions 22*d* is released, and at the same time, the temporary stop of the optical portion 8 is also released. Therefore, the optical portion 8 starts moving again.

Next, the optical portion 8 moves forward while being guided by the left and right second guide surfaces 22*b*. In this case, the distance between the left and right second guide surfaces 22*b* is gradually decreased toward the front, and accordingly, the space inside of the injection tube 4 is also gradually narrowed. Therefore, when the intraocular lens 7 is pushed out by the rod portion 18, the optical portion 8 is gradually bent while being guided by the left and right second guide surfaces 22*b*, and ultimately it is rounded small and folded. At that time, when the tip end part of the support portion 9*b* rides on the surface of the optical portion 8, the optical portion 8 is likely to bend in a direction to embrace the support portion 9*b*. The reason is that the optical portion 8 is easily deformed to the side on which the support portion 9*b* is placed, whereas the optical portion 8 is hardly deformed on the opposite side. Therefore, even when the optical portion 8 starts to move at an earlier timing than expected, the direction in which the optical portion 8 is bent can be determined in one direction (the direction in which the support portion 9*b* is embraced).

Figure 20A:
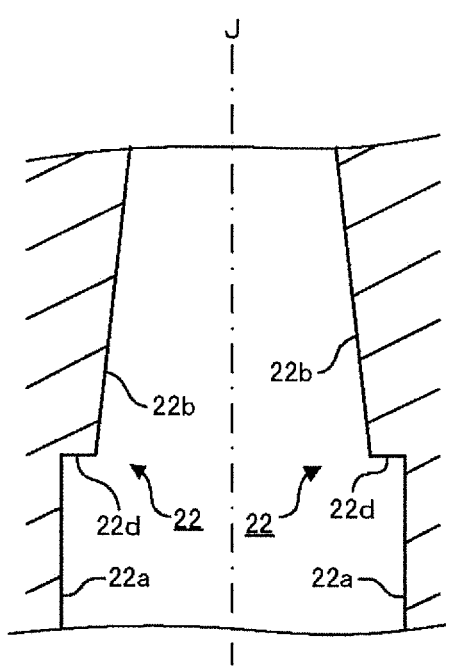
FIGS. 20A to 20D are views showing an example of the structure of a protrusion according to a fourth embodiment of the present invention.
Figure 20B:
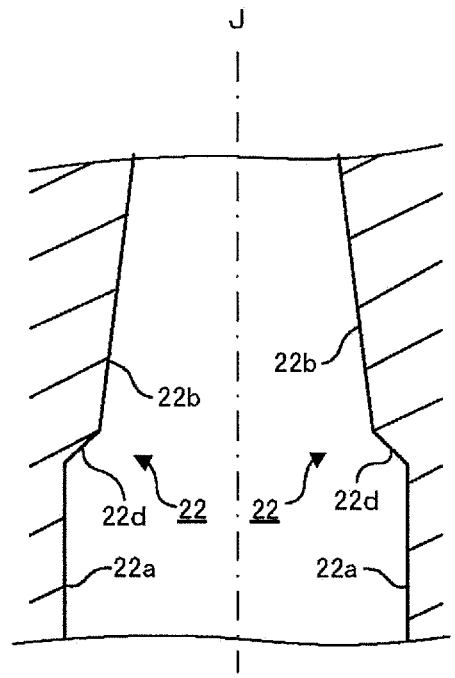
Figure 20C:
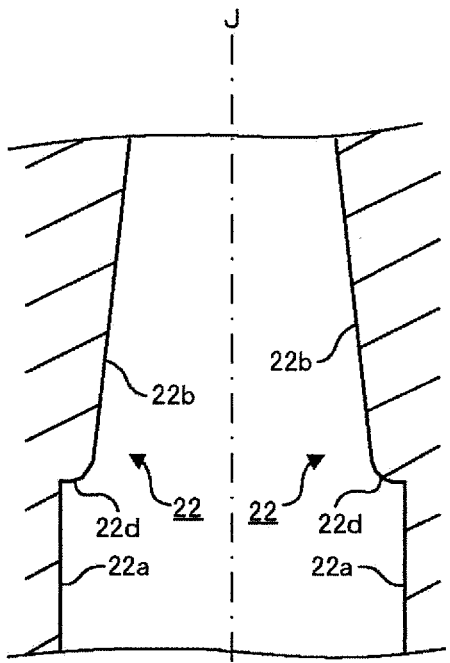
Figure 20D:
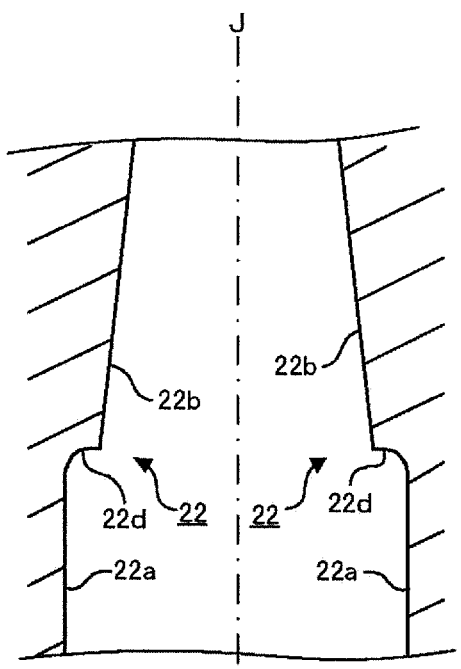

In the fourth embodiment, any structure may be adopted as long as the structure of the protrusion 22*d* is such that the optical portion 8 can be temporarily stopped. For example, the protrusion 22*d* may be formed so as to form a right angle with respect to the first guide surface 22*a* as shown in FIG. 20A, or the protrusion 22*d* may be formed so as to form an obtuse angle with respect to the first guide surface 22*a* as shown in FIG. 20B, or the projecting portion 22*d* may be formed in a round shape from the first guide surface 22*a* to the second guide surface 22*b* as shown in FIGS. 20C and 20D.

Further, in the fourth embodiment, the protrusion 22*d* is formed at the joint portion 22*c* between the first guide surface 22*a* and the second guide surface 22*b*. However, the present invention is not limited thereto, and the protrusion 22*d* may be formed in the middle of the first guide surface 22*a* or in the middle of the second guide surface 22*b* for the same purpose as described above.

6. Modified Example, Etc

The technical scope of the present invention is not limited to the embodiments described above but includes various modifications and improvements within the scope of deriving specific effects obtained by the constituent features of the invention and combinations thereof.

For example, in the abovementioned each embodiment, the preload type intraocular lens injector 1 is given as an example. However, the present invention is not limited thereto, and the present invention may be applied to an intraocular lens injector of the type in which the user using the intraocular lens injector sets the intraocular lens each time.

Further, in the abovementioned each embodiment, the pushing member 5 is moved forward by the rotating operation of the operation portion 3. However, the present invention is not limited thereto, and it is also acceptable to adopt a structure in which the pushing member is pushed directly using a finger.

Further, in the abovementioned each embodiment, the rod portion 18 of the pushing member 5 is configured to be elastically deformable, and when the pushing member 5 is moved forward, the tip end part of the rod portion 18 is displaced in a predetermined direction (vertical direction, left-right direction) by the elastic deformation of the rod portion 18. However, the present invention is not limited thereto, and for example it is also acceptable to adopt a structure in which the plunger portion 17 and the rod portion 18 are connected to each other and the rod portion 18 is rotatably supported by the joint portion between the plunger portion 17 and the rod portion 18.

Further, in the abovementioned each embodiment, in order to limit the vertical displacement amount of the optical portion 8, a pair of right and left recessed grooves are formed in the lens setting portion 6. However, the other structure may be acceptable. For example, although not shown, when a pair of left and right pressing portions are formed inside of the injection tube 4 and the injection tube 4 is attached with the intraocular lens 7 set on the lens setting portion 6, the pressing portions may be disposed above the right and left outer peripheral parts of the optical portion 8 interposing an appropriate gap. In the second embodiment (FIGS. 9 to 12B), the following structure is adopted for your reference: a pressing portion 16 is formed inside of the injection tube 4 and the vertical displacement amount of the optical portion 8 is limited by the pressing portion 16.

Further, the abovementioned first embodiment and the second embodiment adopt a structure in which the tip end portion of the rod portion 18 is displaced in the vertical direction, and the third embodiment adopt a structure in which the tip end portion of the rod portion 18 is displaced in the left-right direction. However, the present invention is not limited thereto, and for example it is also acceptable to adopt a structure in which the tip end portion of the rod portion 18 is displaced in both the vertical direction and the left-right direction by appropriately combining the above embodiments. By adopting this structure, it is possible to more surely place the tip end portion of the support portion 9b on the surface of the optical portion 8.

Further, in the abovementioned third embodiment, the guide groove 21 is curved in the right direction Y1 at a part from the starting point 21a to the middle point 21c of the guide groove 21. However, the present invention is not limited thereto, and the starting point 21a of the guide groove 21 may be disposed deviated in the rightward direction Y1 from the central axis J, and a part extending from the starting point 21a to the middle point 21c may be formed straight along the central axis J. When this structure is adopted, at a position deviated in the rightward direction Y1 from the central axis J, the tip end part of the rod portion 18 moves straight through a part from the starting point 21a to the middle point 21c of the guide groove 21, and moves through a part from the middle point 21c to the end point 21b of the guide groove 21 while displacing in the left direction Y2.

Further, in the abovementioned first to third embodiments, explanation is given for a structure of directly guiding the movement of the tip end part of the rod portion 18 by the guide slopes 11, 12, the grooves 13, 14, the guide groove 21, or the like, as the guide mechanism for guiding the movement of the pushing member 5. However, the present invention is not limited thereto, and it is also acceptable to adopt a structure of indirectly guiding the movement of the tip end part of the rod portion 18 by contact with a part other than the tip end part of the rod portion 18 (for example, a middle point side or a base end side of the rod portion 18).

Further, the abovementioned characteristic structures of the first to fourth embodiments can be combined with each other as long as there is no particular problem.

Further, the structure of the fourth embodiment may be applied to an intraocular lens injector not including the guide mechanism of guiding the movement of the pushing member. Preferable aspects in this case are supplementary described as follows.

Supplementary Description 1

There is provided an intraocular lens injector configured to inject an intraocular lens having an optical portion and support portions extending from the optical portion into an eye, including:

an injector main body having a lens setting portion on which the intraocular lens is set;

a pushing member that pushes out the intraocular lens from the lens setting portion by moving in a direction of a central axis of the injector main body; and a pair of left and right side wall guides that guide a movement of the optical portion of the intraocular lens pushed out from the lens setting portion by the pushing member, wherein the pair of right and left side wall guides has a guide surface for guiding the optical portion of the intraocular lens pushed out from the lens setting portion by the pushing member, and has a protrusion for temporarily stopping the optical portion moving along the guide surface.

Supplementary Description 2

The intraocular lens injector of the supplementary description 1, wherein a movement start position at which the optical portion of the intraocular lens starts moving is set in the lens setting portion, and the protrusion is disposed so as to come into contact with the optical portion when the optical portion is moved by a predetermined amount from the movement start position.

Supplementary Description 3

The intraocular lens injector of the supplementary description 2, wherein the predetermined amount is 0.5 mm or more and 1.0 mm or less.

Supplementary Description 4

The intraocular lens injector of any one of the supplementary descriptions 1 to 3, wherein a protruding dimension of the protrusion is 0.1 mm or more and 0.5 mm or less.

DESCRIPTION OF SIGNS AND NUMERALS

1 Intraocular lens injector
2 Injector main body
3 Operation portion
4 Injection tube
5 Pushing member
6 Lens setting portion
7 Intraocular lens
8 Optical portion
9a Support portion (front support portion)
9b Support portion (rear support portion)
11 Guide slope (lower guide slope)
12 Upper guide slope
13 Lower groove
14 Upper groove
18 Rod portion
21 Guide groove
22 Side wall guide
22a First guide surface
22b Second guide surface
22c Joint portion
22d Protrusion

The invention claimed is:

1. An intraocular lens injector configured to inject an intraocular lens having an optical portion with a peripheral edge and support portions having tip end parts extending from the optical portion into an eye, the intraocular lens injector comprising:

an injector main body having a central axis and a lens setting portion on which the intraocular lens is set;

a pushing member, having a tip end part, that pushes out the intraocular lens from the lens setting portion by moving in a direction of the central axis of the injector main body; and a guide mechanism that guides the movement of the pushing member when the pushing member moves in the direction of the central axis of the injector main body such that the tip end part of the pushing member is displaced in a direction intersecting the central axis of the injector main body, the guide mechanism including a lower guide slope having an inclined portion inclined obliquely upward from an upstream side to a downstream side in a moving direction of the pushing member and an upper guide slope having an inclined portion inclined obliquely downward from the upstream side to the downstream side in the moving direction of the pushing member, wherein when the pushing member moves in the direction of the central axis of the injector main body, the tip end part of the pushing member comes into contact with one of the support portions of the intraocular lens and pushes the contacted support portion over the optical portion prior to any folding of the optical portion, and thereafter comes into contact with the optical portion while pushing the contacted support portion; and the tip end part of the pushing member is displaced in a vertical direction along the lower and upper guide slopes.

2. The intraocular lens injector according to claim 1, wherein the guide mechanism guides the movement of the pushing member so that the tip end part of the pushing member pushes the contacted support portion while being displaced upward.

3. The intraocular lens injector according to claim 1, wherein the guide mechanism includes a restraining portion that suppresses a lateral shake of the tip end part of the pushing member that moves in the direction of the central axis of the injector main body.

4. The intraocular lens injector according to claim 1, further comprising:

a pair of left and right side wall guides that guide the movement of the optical portion of the intraocular lens pushed out from the lens setting portion by the pushing member, wherein the pair of left and right side wall guides have a guide surface for guiding the optical portion of the intraocular lens pushed out from the lens setting portion by the pushing member, and have a protrusion for temporarily stopping the optical portion moving along the guide surface.

5. The intraocular lens injector according to claim 4, wherein a movement start position at which the optical portion of the intraocular lens starts moving is set in the lens setting portion, and the protrusion is disposed so as to come into contact with the optical portion when the optical portion is moved by a predetermined amount from the movement start position.

6. The intraocular lens injector according to claim 5, wherein the predetermined amount is from 0.5 mm to 1.0 mm.

7. The intraocular lens injector according to claim 4, wherein a protruding dimension of the protrusion is from 0.1 mm to 0.5 mm.

8. The intraocular lens injector according to claim 1, wherein the intraocular lens is a pre-load type in which the intraocular lens is preset on the lens setting portion.

9. The intraocular lens injector according to claim 1, wherein the intraocular lens is set on the lens setting portion in a no-load state.

10. An intraocular lens injector configured to inject an intraocular lens having an optical portion with a peripheral edge and support portions having tip end parts extending from the optical portion into an eye, the intraocular lens injector comprising:

an injector main body having a central axis and a lens setting portion on which the intraocular lens is set;

a pushing member, having a tip end part, that pushes out the intraocular lens from the lens setting portion by moving in a direction of the central axis of the injector main body; and a guide mechanism including a guide groove that guides the movement of the pushing member when the pushing member moves in the direction of the central axis of the injector main body such that the tip end part of the pushing member is displaced in a left-right direction, wherein the tip end part of the pushing member is displaced in a left-right direction along the guide groove;

when the pushing member moves in the direction of the central axis of the injector main body, the tip end part of the pushing member comes into contact with one of the support portions of the intraocular lens and pushes the contacted support portion over the optical portion prior to any folding of the optical portion, and thereafter comes into contact with the optical portion while pushing the contacted support portion; and the guide mechanism guides the movement of the pushing member, so that the tip end part of the pushing member comes into contact with the tip end part of the contacted support portion at a position deviated from a position of the central axis of the injector main body in one of the left and right directions, and thereafter the tip end part of the pushing member is displaced to the other side in the left-right direction and comes into contact with the optical portion at the position of the central axis of the injector main body.

11. A preloaded intraocular lens injector, comprising:

an injector main body having a lens setting portion, an inner surface, a nozzle and a central axis;

an intraocular lens loaded in the lens setting portion and having an optical portion with a peripheral edge and first and second support portions that have respective tip ends, the first support portion extending forwardly from the optical portion and the second support portion extending rearwardly from the optical portion and over the inner surface;

a rod, movable along inner surface in the direction of the central axis, defining a tip end and including first and second contact portions at the tip end; and a guide slope, located under the second support portion and inclined obliquely upward, that displaces the rod upwardly away from the inner surface as the rod moves toward the nozzle;

wherein the intraocular lens, the lens setting portion, the rod and the guide slope are respectively configured and arranged relative to one another such that as the rod moves toward the nozzle, and prior to any folding of the optical portion, the first contact portion will engage the second support portion tip end, the rod tip end will thereafter engage the guide slope and be displaced upwardly, thereby displacing the second support portion tip end upwardly, and the second contact portion will thereafter engage the optical portion peripheral edge as the second support portion tip end passes over the optical portion peripheral edge.

12. A preloaded intraocular lens injector as claimed in claim 11, further comprising:
a plunger connected to the rod.

13. A preloaded intraocular lens injector as claimed in claim 11, further comprising:
a restraining portion that suppresses a lateral shake of the rod tip end as the rod moves toward the nozzle.

14. A preloaded intraocular lens injector as claimed in claim 11,
wherein the guide slope comprises a lower guide slope; and
the intraocular lens injector further comprises an upper guide slope inclined obliquely downward.

15. A preloaded intraocular lens injector, comprising:
an injector main body having a lens setting portion, a nozzle and a central axis;
an intraocular lens loaded in the lens setting portion and having an optical portion with a peripheral edge and first and second support portions that have respective tip ends, the first support portion extending forwardly from the optical portion and the second support portion extending rearwardly from the optical portion;
a rod, movable in the direction of the central axis, defining a tip end and including first and second contact portions at the tip end; and
a guide groove, a part of which is located under the second support portion, that displaces the rod tip end from the central axis in one of a left direction and a right direction and back to the central axis in the other of the left direction and the right direction as the rod moves toward the nozzle;
wherein the intraocular lens, the lens setting portion, the rod and the guide groove are respectively configured and arranged relative to one another such that as the rod moves toward the nozzle, and prior to any folding of the optical portion, the rod tip end will be displaced from the central axis in one of the left direction and the right direction, the first contact portion will thereafter engage the second support portion tip end, the rod tip end will thereafter be displaced back to the central axis in the other of the left direction and the right direction, and the second contact portion will thereafter engage the optical portion peripheral edge as the second support portion tip end passes over the optical portion peripheral edge.

16. A preloaded intraocular lens injector as claimed in claim 15, further comprising:
a plunger connected to the rod.

* * * * *